United States Patent
Magnenat et al.

(10) Patent No.: US 9,567,398 B2
(45) Date of Patent: Feb. 14, 2017

(54) ANTIBODY WITH SPECIFICITY FOR GM-CSF (II)

(75) Inventors: Laurent Magnenat, Nyon (CH); Olivier Leger, Saint-Sixt (FR); Charles MacKay, Prahran (AU); David Georges Zahra, West Pennant Hills (AU)

(73) Assignee: MERCK SERONO S.A., Coinsins, Vaud (CH)

( * ) Notice: Subject to any disclaimer, the term of this patent is extended or adjusted under 35 U.S.C. 154(b) by 0 days.

(21) Appl. No.: 13/988,498

(22) PCT Filed: Nov. 17, 2011

(86) PCT No.: PCT/EP2011/070375
§ 371 (c)(1),
(2), (4) Date: May 20, 2013

(87) PCT Pub. No.: WO2012/066089
PCT Pub. Date: May 24, 2012

(65) Prior Publication Data
US 2014/0065163 A1 Mar. 6, 2014

(30) Foreign Application Priority Data
Nov. 18, 2010 (EP) .................................... 10191664

(51) Int. Cl.
*A61K 39/395* (2006.01)
*A61K 39/00* (2006.01)
*C07K 16/24* (2006.01)
*C12N 15/00* (2006.01)

(52) U.S. Cl.
CPC ......... *C07K 16/243* (2013.01); *C07K 2317/24* (2013.01); *C07K 2317/33* (2013.01); *C07K 2317/55* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| AU | WO 2008141391 A1 | * 11/2008 | ........... C07K 16/243 |
|---|---|---|---|
| WO | 2008141391 A1 | 11/2008 | |
| WO | 2009038760 A2 | 3/2009 | |
| WO | 2009062238 A1 | 5/2009 | |

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Altschul, Stephen F. et al, "Gapped BLAST and PSI-BLAST: a new generation of protein database search programs," Nucleic Acids Research (1997), vol. 25, No. 17, pp. 3389-3402.
Birney, Ewan et al., "GeneWise and Genomewise," Genome Research (2004), vol. 14, pp. 988-995.
Greenfield, Edward A. (Editor), Antibodies: A Laboratory Manual (2nd Ed., 1988), Cold Spring Harbor Laboratory Press.
Kabat, Elvin A. et al., "Sequences of Proteins of Immunological Interest," (5th Ed., 1991), U.S. Department of Health and Human Services, Public Health Service, National Institutes of Health, NIH Publication No. 91-3242.
Sambrook, Joseph et al., "Molecular Cloning," (3rd Ed., 2001), Cold Spring Harbor Laboratory Press.
International Search Report and Written Opinion of PCT/EP2011/070375 filed Nov. 17, 2011.

* cited by examiner

*Primary Examiner* — Christine J Saoud
*Assistant Examiner* — Jegatheesan Seharaseyon
(74) *Attorney, Agent, or Firm* — Arent Fox LLP

(57) ABSTRACT

The present invention relates to antibodies with specificity for granulocyte-macrophage colony stimulating factor (GM-CSF). More particularly, the invention relates to humanized monoclonal antibodies that bind specifically to human GM-CSF with high affinity. The invention also relates to nucleic acids encoding the antibodies, vectors for expression of these nucleic acids, and host cells for producing said antibodies. Further, the invention relates to the use of said antibodies in the diagnosis or treatment of autoimmune or inflammatory diseases.

20 Claims, 17 Drawing Sheets

Sequence alignment human GM-CSF SNPs:

```
HUMAN-GMCSF-I117    MWLQSLLLLGTVACSISAPARSPSPSTQPWEHVNAIQEARRLLNLSRDTAAEMNETVEVI
HUMAN-GMCSF-T117    MWLQSLLLLGTVACSISAPARSPSPSTQPWEHVNAIQEARRLLNLSRDTAAEMNETVEVI
                    ************************************************************

HUMAN-GMCSF-I117    SEMFDLQEPTCLQTRLELYKQGLRGSLTKLKGPLTMMASHYKQHCPPTPETSCATQIITF
HUMAN-GMCSF-T117    SEMFDLQEPTCLQTRLELYKQGLRGSLTKLKGPLTMMASHYKQHCPPTPETSCATQTITF
                    ******************************************************** ***

HUMAN-GMCSF-I117    ESFKENLKDFLLVIPFDCWEPVQE   (SEQ ID NO:26)
HUMAN-GMCSF-T117    ESFKENLKDFLLVIPFDCWEPVQE   (SEQ ID NO:27)
                    ************************
```

Figure 1a)

Sequence alignment GM-CSF orthologs

```
HUMAN      MWLQSLLLLGTVACSISAPARSPSPSTQPWEHVNAIQEARRLLNLSRDTAAEMNETVEVI
MACACA     MWLQGLLLLLGTVACSISAPARSPSPGTQPWEHVNAIQEARRLLNLSRDTAAEMNKTVEVV
MARMOSET   MWLQNLLLLGTVAGSISAPTHLPSPDTQPSKHVNAIQEAQRLLNLSRDTAPETNETVEVV
           ****.********** **** : **.***:.******* ****** *.* .* :****:

HUMAN      SEMFDLQEPTCLQTRLELYKQGLRGSLTKLKGPLTMMASHYKQHCPPTPETSCATQIITF
MACACA     SEMFDLQEPSCLQTRLELYKQGLQGSLTKLKLGPLTMMASHYKQHCPPTPETSCATQIITF
MARMOSET   SEMFDRQEPTCLQTRLELYKESLWGSLTKLKGLLTMIASHYKQHCPPTLETSCATKIITF
           ***** ***:********: :* ****** ***:*********** ****:****  (SEQ ID NO:26)

HUMAN      ESFKENLKDFLLVIPFDCWEPVQE                              (SEQ ID NO:26)
MACACA     QSFKENLKDFLLVIPFDCWEPVQE                              (SEQ ID NO:29)
MARMOSET   ESFKENLKDFLLAIPVDCWDPVQE                              (SEQ ID NO:30)
           :************.**:***:***

Sequences (1:2) Aligned. Score: 95.1389
Sequences (1:3) Aligned. Score: 84.0278
Sequences (2:3) Aligned. Score: 82.6389
```

Figure 1b)

Heavy chain:

```
                                           CDR1                                    S55/S56
                                                                                   CDR2
IGHV3-7    EVQLVESGGGLVQPGGSLRLSCAASGFTFSSYWMSWVRQAPGKGLEWVANIKQDGSEKYY
4K21-mVH   EVQLVESGGGLVKSGGSLKLSCAASGFAFSAYDMSWVRQTPEKRLELVAYISSGGSSFYY
4K21-hVH   EVQLVESGGGLVQPGGSLRLSCAASGFAFSAYDMSWVRQAPGKRLELVAYISSGGSSFYY
           *********** :.**:***:******. *:**:****** ::**:***:*****.***
                    10        20        30        40        50   52 :   55
                                                                   52a 53
             T62
                                                               CDR3
IGHV3-7    VDSVKGRFTISRDNAKNSLYLQMNSLRAEDTAVYYCAR
4K21-mVH   PDTVKGRFTISRDNAKNTLYLQMSSLKSEDTAMYYCTRHLGFDYWGQGTTLTVSS
4K21-hVH   PDTVKGRFTISRDNAKNSLYLQMNSLRAEDTAVYYCTRHLGFDYWGQGTLVTVSS
           .*:*************.****:.**::****:****:*                        (SEQ ID NO:24)
           *--: ---- ----- ----: -----------:**********************     (SEQ ID NO:17)
              60        70        80        90       100       110    (SEQ ID NO:18)
                             82a 82b 82c
```

Light chain:

```
                   S27e/N28      H34
                         CDR1                                       N53
                                                                    CDR2
IGKV2-28   DIVMTQSPLSLPVTPGEPASISCRSSQSLLHSNGYNYLDWYLQKPGQSPQLLIYLGSNRA
4K21-mVL   DVVMTQTPLSLPVSLGDQASISCRSSQSLVNSNGNTYLHWFLQKPGQSPKLLIYKVSNRF
4K21-hVL   DIVMTQSPLSLPVTPGEPASISCRSSQSLVNSNGNTYLHWYLQKPGQSPQLLIYKVSNRF
           *:****:******:.*:.******** **:: *** ***.*:.*********:****:.***
                   10        20   27:  28 30       40        50
                                   27a        H93
                                   27e        CDR3
IGKV2-28   SGVPDRFSGSGSGTDFTLKISRVEAEDVGVYYCMQALQTP                    (SEQ ID NO:25)
4K21-mVL   SGSPDRFSGSGSGTDFTLKISRVEAEDLGVYFCSQSTHVPPTFGGGTKLEIK        (SEQ ID NO:19)
4K21-hVL   SGVPDRFSGSGSGTDFTLKISRVEAEDVGVYYCSQSTHVPPTFGQGTKVEIK        (SEQ ID NO:20)
           **.***************************:**:: :*:
              56      60        70        80        90       100
```

Figure 2

Heavy chains:

```
                                                                                      S55K/R-S56V
4K21-hVH              EVQLVESGGGLVQPGGSLRLSCAASGFAFSAYDMSWVRQAPGKRLELVAYISSGGSSFYY
4K21-hVH-S55K-T62S    EVQLVESGGGLVQPGGSLRLSCAASGFAFSAYDMSWVRQAPGKRLELVAYISSGGKSFYY    (SEQ ID NO:18)
4K21-hVH-S55R-T62S    EVQLVESGGGLVQPGGSLRLSCAASGFAFSAYDMSWVRQAPGKRLELVAYISSGGRSFYY    (SEQ ID NO:21)
4K21-hVH-S56V-T62S    EVQLVESGGGLVQPGGSLRLSCAASGFAFSAYDMSWVRQAPGKRLELVAYISSGGSVFYY    (SEQ ID NO:22)
                      ************************************************:***         (SEQ ID NO:23)
                      1         10        20        30        40        50 52a 55

4K21-hVH              PDTVKGRFTISRDNAKNSLYLQMNSLRAEDTAVYYCTRHLGFDYWGQGTLVTVSS
4K21-hVH-S55K-T62S    PDSVKGRFTISRDNAKNSLYLQMNSLRAEDTAVYYCTRHLGFDYWGQGTLVTVSS
4K21-hVH-S55R-T62S    PDSVKGRFTISRDNAKNSLYLQMNSLRAEDTAVYYCTRHLGFDYWGQGTLVTVSS
4K21-hVH-S56V-T62S    PDSVKGRFTISRDNAKNSLYLQMNSLRAEDTAVYYCTRHLGFDYWGQGTLVTVSS
                      **:****************************************************
                      60        70        80 82a 82c  90        100       110
                      1 T62S
```

Light chains:

```
                                                             S27eY-N28I  H34S
4K21-hVL                            DIVMTQSPLSLPVTPGEPASISCRSSQSLVNSNGNTYLHWYLQKPGQSPQ
4K21-hVL-S27eY-N28I-H34S-N53R-H93Y  DIVMTQSPLSLPVTPGEPASISCRSSQSLVNYIGNTYLSWYLQKPGQSPQ
4K21-hVL-N28I-H34S-N53R-H93Y        DIVMTQSPLSLPVTPGEPASISCRSSQSLVNSIGNTYLSWYLQKPGQSPQ
                                    ******************************:: .*****************
                                    1         10        20    27 27a 27e 28  30      40    H93Y
                                                                                           90

N53R                                         H93Y
4K21-hVL                            LLIYKVSNRFSGVPDRFSGSGSGTDFTLKISRVEAEDVGVYYCSQSTHVP
4K21-hVL-S27eY-N28I-H34S-N53R-H93Y  LLIYKVSRRFSGVPDRFSGSGSGTDFTLKISRVEAEDVGVYYCSQSTYVP
4K21-hVL-N28I-H34S-N53R-H93Y        LLIYKVSRRFSGVPDRFSGSGSGTDFTLKISRVEAEDVGVYYCSQSTYVP
                                    *******.*********************************.******:**
                                    46        50        60        70        80

4K21-hVL                            PTFGQGTKVEIK    (SEQ ID NO:20)
4K21-hVL-S27eY-N28I-H34S-N53R-H93Y  PTFGQGTKVEIK    (SEQ ID NO:9)
4K21-hVL-N28I-H34S-N53R-H93Y        PTFGQGTKVEIK    (SEQ ID NO:10)
                                    ************
                                    96        100
```

Figure 4

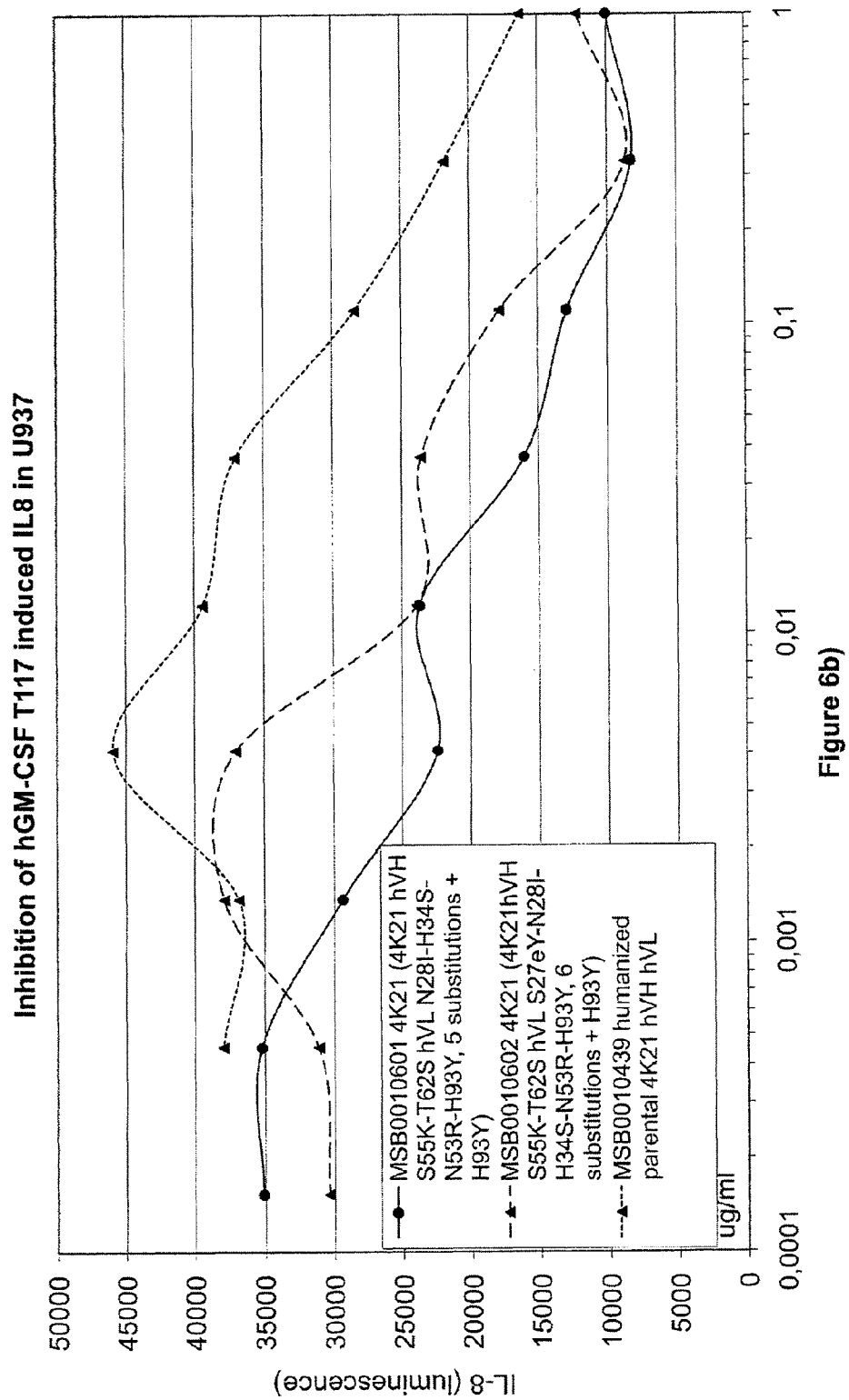

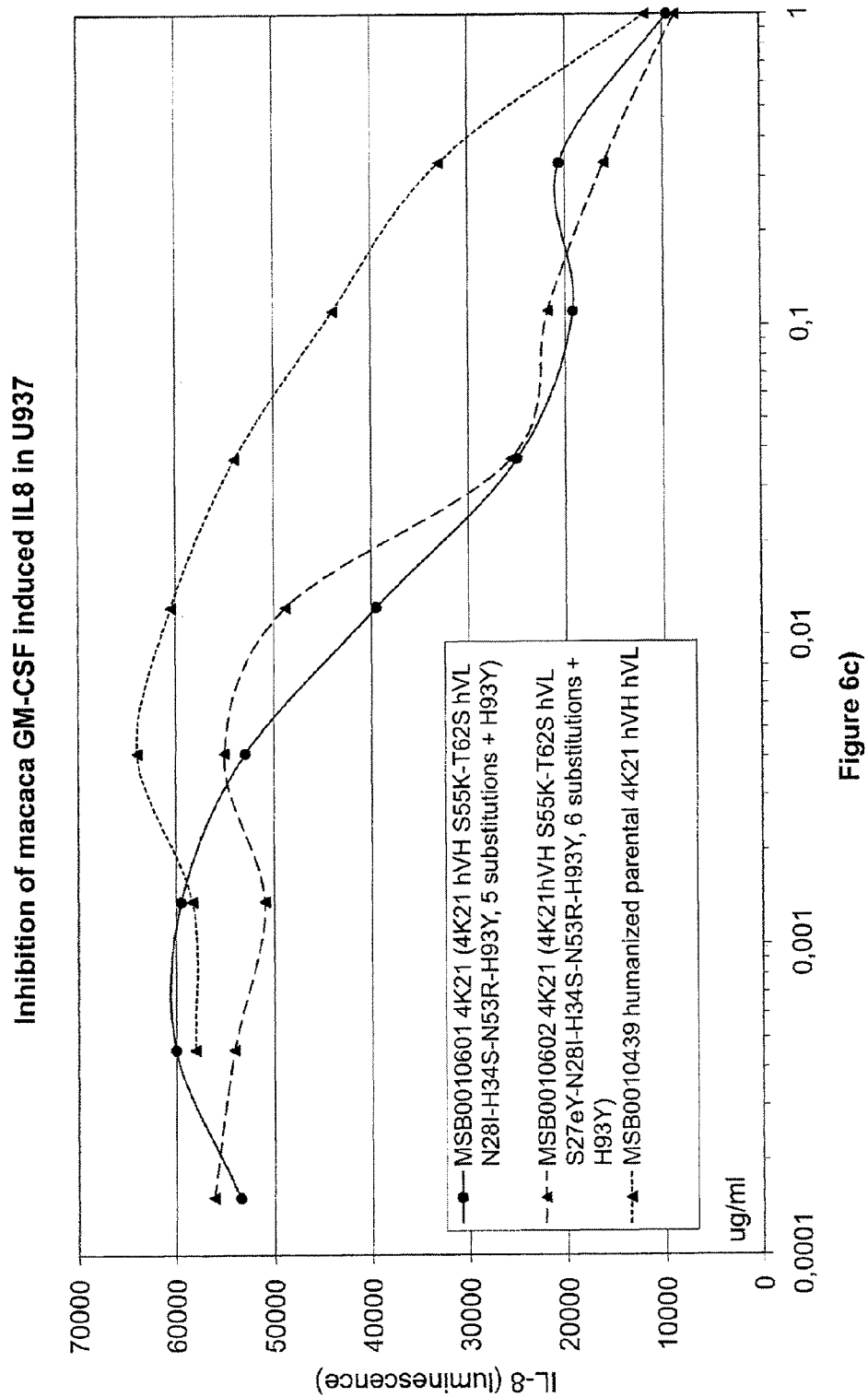

SEQUENCE LISTING

```
<160> NUMBER OF SEQ ID NOS: 44

<210> SEQ ID NO 1
<211> LENGTH: 5
<212> TYPE: PRT
<213> ORGANISM: Eutheria
<220> FEATURE:
<221> NAME/KEY: MISC_FEATURE
<222> LOCATION: (1)..(5)
<223> OTHER INFORMATION: 4K21 heavy chain CDR1

<400> SEQUENCE: 1

Ala Tyr Asp Met Ser
1               5

<210> SEQ ID NO 2
<211> LENGTH: 17
<212> TYPE: PRT
<213> ORGANISM: Eutheria
<220> FEATURE:
<221> NAME/KEY: MISC_FEATURE
<222> LOCATION: (1)..(17)
<223> OTHER INFORMATION: 4K21 heavy chain CDR2

<400> SEQUENCE: 2

Tyr Ile Ser Ser Gly Gly Ser Ser Phe Tyr Tyr Pro Asp Thr Val Lys
1               5                   10                  15

Gly

<210> SEQ ID NO 3
<211> LENGTH: 6
<212> TYPE: PRT
<213> ORGANISM: Eutheria
<220> FEATURE:
<221> NAME/KEY: MISC_FEATURE
<222> LOCATION: (1)..(6)
<223> OTHER INFORMATION: 4K21 heavy chain CDR3

<400> SEQUENCE: 3

His Leu Gly Phe Asp Tyr
1               5

<210> SEQ ID NO 4
<211> LENGTH: 16
<212> TYPE: PRT
<213> ORGANISM: Eutheria
<220> FEATURE:
<221> NAME/KEY: MISC_FEATURE
<222> LOCATION: (1)..(16)
<223> OTHER INFORMATION: 4K21 light chain CDR1

<400> SEQUENCE: 4

Arg Ser Ser Gln Ser Leu Val Asn Ser Asn Gly Asn Thr Tyr Leu His
1               5                   10                  15

<210> SEQ ID NO 5
<211> LENGTH: 7
<212> TYPE: PRT
<213> ORGANISM: Eutheria
<220> FEATURE:
<221> NAME/KEY: MISC_FEATURE
<222> LOCATION: (1)..(7)
<223> OTHER INFORMATION: 4K21 light chain CDR2

<400> SEQUENCE: 5

Lys Val Ser Asn Arg Phe Ser
1               5
```

```
<210> SEQ ID NO 6
<211> LENGTH: 9
<212> TYPE: PRT
<213> ORGANISM: Artificial
<220> FEATURE:
<223> OTHER INFORMATION: 4K21 light chain CDR3 with H93Y mutation

<400> SEQUENCE: 6

Ser Gln Ser Thr Tyr Val Pro Pro Thr
1               5

<210> SEQ ID NO 7
<211> LENGTH: 9
<212> TYPE: PRT
<213> ORGANISM: Eutheria
<220> FEATURE:
<221> NAME/KEY: MISC_FEATURE
<222> LOCATION: (1)..(9)
<223> OTHER INFORMATION: 4K21 light chain CDR3

<400> SEQUENCE: 7

Ser Gln Ser Thr His Val Pro Pro Thr
1               5

<210> SEQ ID NO 8
<211> LENGTH: 112
<212> TYPE: PRT
<213> ORGANISM: Artificial
<220> FEATURE:
<223> OTHER INFORMATION: humanized 4K21 variable region light chain with
      H93 mutation (4K21 hVL-H93Y)

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asn Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Tyr Val Pro Pro Thr Phe Gly Gln Gly Thr Lys Val Glu Ile Lys
            100                 105                 110

<210> SEQ ID NO 9
<211> LENGTH: 112
<212> TYPE: PRT
<213> ORGANISM: Artificial
<220> FEATURE:
<223> OTHER INFORMATION: humanized 4K21 variable region light chain with
      mutations (4K21 hVL-S27eY-N28I-H34S-N53R-H93Y)

<400> SEQUENCE: 9

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asn Tyr
            20                  25                  30

Ile Gly Asn Thr Tyr Leu Ser Trp Tyr Leu Gln Lys Pro Gly Gln Ser
        35                  40                  45
```

```
Pro Gln Leu Leu Ile Tyr Lys Val Ser Arg Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Tyr Val Pro Pro Thr Phe Gly Gln Gly Thr Lys Val Glu Ile Lys
            100                 105                 110
```

<210> SEQ ID NO 10
<211> LENGTH: 112
<212> TYPE: PRT
<213> ORGANISM: Artificial
<220> FEATURE:
<223> OTHER INFORMATION: humanized 4K21 variable region light chain with
      mutations (4K21 hVL-N28I-H34S-N53R-H93Y)

<400> SEQUENCE: 10

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Asn Ser
                20                  25                  30

Ile Gly Asn Thr Tyr Leu Ser Trp Tyr Leu Gln Lys Pro Gly Gln Ser
            35                  40                  45

Pro Gln Leu Leu Ile Tyr Lys Val Ser Arg Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Tyr Val Pro Pro Thr Phe Gly Gln Gly Thr Lys Val Glu Ile Lys
            100                 105                 110
```

<210> SEQ ID NO 11
<211> LENGTH: 17
<212> TYPE: PRT
<213> ORGANISM: Artificial
<220> FEATURE:
<223> OTHER INFORMATION: 4K21 heavy chain CDR2 with S55K & T62S
      mutations

<400> SEQUENCE: 11

```
Tyr Ile Ser Ser Gly Gly Lys Ser Phe Tyr Tyr Pro Asp Ser Val Lys
 1               5                  10                  15

Gly
```

<210> SEQ ID NO 12
<211> LENGTH: 17
<212> TYPE: PRT
<213> ORGANISM: Artificial
<220> FEATURE:
<223> OTHER INFORMATION: 4K21 heavy chain CDR2 with S55R & T62S
      mutations

<400> SEQUENCE: 12

```
Tyr Ile Ser Ser Gly Gly Arg Ser Phe Tyr Tyr Pro Asp Ser Val Lys
 1               5                  10                  15

Gly
```

<210> SEQ ID NO 13

-continued

```
<211> LENGTH: 17
<212> TYPE: PRT
<213> ORGANISM: Artificial
<220> FEATURE:
<223> OTHER INFORMATION: 4K21 heavy chain CDR2 with S56V & T62S
      mutations

<400> SEQUENCE: 13

Tyr Ile Ser Ser Gly Gly Ser Val Phe Tyr Tyr Pro Asp Ser Val Lys
1               5                   10                  15

Gly

<210> SEQ ID NO 14
<211> LENGTH: 16
<212> TYPE: PRT
<213> ORGANISM: Artificial
<220> FEATURE:
<223> OTHER INFORMATION: 4K21 light chain CDR1 with N28I & H34S
      mutations

<400> SEQUENCE: 14

Arg Ser Ser Gln Ser Leu Val Asn Ser Ile Gly Asn Thr Tyr Leu Ser
1               5                   10                  15

<210> SEQ ID NO 15
<211> LENGTH: 16
<212> TYPE: PRT
<213> ORGANISM: Artificial
<220> FEATURE:
<223> OTHER INFORMATION: 4K21 light chain CDR1 with S27eY, N28I & H34S
      mutations

<400> SEQUENCE: 15

Arg Ser Ser Gln Ser Leu Val Asn Tyr Ile Gly Asn Thr Tyr Leu Ser
1               5                   10                  15

<210> SEQ ID NO 16
<211> LENGTH: 7
<212> TYPE: PRT
<213> ORGANISM: Artificial
<220> FEATURE:
<223> OTHER INFORMATION: 4K21 light chain CDR2 with N53R mutation

<400> SEQUENCE: 16

Lys Val Ser Arg Arg Phe Ser
1               5

<210> SEQ ID NO 17
<211> LENGTH: 115
<212> TYPE: PRT
<213> ORGANISM: Mus musculus
<220> FEATURE:
<221> NAME/KEY: MISC_FEATURE
<222> LOCATION: (1)..(115)
<223> OTHER INFORMATION: mouse 4K21 variable region heavy chain (4K21
      mVH)

<400> SEQUENCE: 17

Glu Val Gln Leu Val Glu Ser Gly Gly Gly Leu Val Lys Ser Gly Gly
1               5                   10                  15

Ser Leu Lys Leu Ser Cys Ala Ala Ser Gly Phe Ala Phe Ser Ala Tyr
            20                  25                  30

Asp Met Ser Trp Val Arg Gln Thr Pro Glu Lys Arg Leu Glu Leu Val
        35                  40                  45

Ala Tyr Ile Ser Ser Gly Gly Ser Phe Tyr Tyr Pro Asp Thr Val
    50                  55                  60
```

```
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                85                  90                  95

Thr Arg His Leu Gly Phe Asp Tyr Trp Gly Gln Gly Thr Thr Leu Thr
            100                 105                 110

Val Ser Ser
        115

<210> SEQ ID NO 18
<211> LENGTH: 115
<212> TYPE: PRT
<213> ORGANISM: Artificial
<220> FEATURE:
<223> OTHER INFORMATION: humanized 4K21 variable region heavy chain
      (4K21 hVH)

<400> SEQUENCE: 18

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Ser Ala Tyr
                20                  25                  30

Asp Met Ser Trp Val Arg Gln Ala Pro Gly Lys Arg Leu Glu Leu Val
            35                  40                  45

Ala Tyr Ile Ser Ser Gly Gly Ser Phe Tyr Tyr Pro Asp Thr Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Thr Arg His Leu Gly Phe Asp Tyr Trp Gly Gln Gly Thr Leu Val Thr
            100                 105                 110

Val Ser Ser
        115

<210> SEQ ID NO 19
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: mouse 4K21 variable region light chain (4K21
      mVL)

<400> SEQUENCE: 19

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val Asn Ser
                20                  25                  30

Asn Gly Asn Thr Tyr Leu His Trp Phe Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95
```

Thr His Val Pro Pro Thr Phe Gly Gly Gly Thr Lys Leu Glu Ile Lys
            100                 105                 110

<210> SEQ ID NO 20
<211> LENGTH: 112
<212> TYPE: PRT
<213> ORGANISM: Artificial
<220> FEATURE:
<223> OTHER INFORMATION: humanized 4K21 variable region light chain
      (4K21 hVL)

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Val Asn Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Val Glu Ile Lys
            100                 105                 110

<210> SEQ ID NO 21
<211> LENGTH: 115
<212> TYPE: PRT
<213> ORGANISM: Artificial
<220> FEATURE:
<223> OTHER INFORMATION: humanized 4K21 variable region heavy chain with
      mutations (4K21 hVH-S55K-T62S)

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ala Tyr
            20                  25                  30

Asp Met Ser Trp Val Arg Gln Ala Pro Gly Lys Arg Leu Glu Leu Val
        35                  40                  45

Ala Tyr Ile Ser Ser Gly Gly Lys Ser Phe Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Leu Gly Phe Asp Tyr Trp Gly Gln Gly Thr Leu Val Thr
            100                 105                 110

Val Ser Ser
        115

<210> SEQ ID NO 22
<211> LENGTH: 115
<212> TYPE: PRT
<213> ORGANISM: Artificial
<220> FEATURE:
<223> OTHER INFORMATION: humanized 4K21 variable region heavy chain with
      mutations (4K21 hVH-S55R-T62S)

-continued

```
<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ala Tyr
            20                  25                  30

Asp Met Ser Trp Val Arg Gln Ala Pro Gly Lys Arg Leu Glu Leu Val
        35                  40                  45

Ala Tyr Ile Ser Ser Gly Gly Arg Ser Phe Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Leu Gly Phe Asp Tyr Trp Gly Gln Gly Thr Leu Val Thr
            100                 105                 110

Val Ser Ser
        115

<210> SEQ ID NO 23
<211> LENGTH: 115
<212> TYPE: PRT
<213> ORGANISM: Artificial
<220> FEATURE:
<223> OTHER INFORMATION: humanized 4K21 variable region heavy chain with
      mutations (4K21 hVH-S56V-T62S)

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ala Tyr
            20                  25                  30

Asp Met Ser Trp Val Arg Gln Ala Pro Gly Lys Arg Leu Glu Leu Val
        35                  40                  45

Ala Tyr Ile Ser Ser Gly Gly Ser Val Phe Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg His Leu Gly Phe Asp Tyr Trp Gly Gln Gly Thr Leu Val Thr
            100                 105                 110

Val Ser Ser
        115

<210> SEQ ID NO 24
<211> LENGTH: 98
<212> TYPE: PRT
<213> ORGANISM: Artificial
<220> FEATURE:
<223> OTHER INFORMATION: IGHV3-7

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45
```

-continued

```
Ala Asn Ile Lys Gln Asp Gly Ser Glu Lys Tyr Tyr Val Asp Ser Val
         50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg

<210> SEQ ID NO 25
<211> LENGTH: 100
<212> TYPE: PRT
<213> ORGANISM: Artificial
<220> FEATURE:
<223> OTHER INFORMATION: IGKV2-28

<400> SEQUENCE: 25

Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu His Ser
                 20                  25                  30
Asn Gly Tyr Asn Tyr Leu Asp Trp Tyr Leu Gln Lys Pro Gly Gln Ser
             35                  40                  45
Pro Gln Leu Leu Ile Tyr Leu Gly Ser Asn Arg Ala Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro
            100

<210> SEQ ID NO 26
<211> LENGTH: 144
<212> TYPE: PRT
<213> ORGANISM: Homo sapiens

<400> SEQUENCE: 26

Met Trp Leu Gln Ser Leu Leu Leu Leu Gly Thr Val Ala Cys Ser Ile
 1               5                  10                  15
Ser Ala Pro Ala Arg Ser Pro Ser Pro Ser Thr Gln Pro Trp Glu His
                 20                  25                  30
Val Asn Ala Ile Gln Glu Ala Arg Arg Leu Leu Asn Leu Ser Arg Asp
             35                  40                  45
Thr Ala Ala Glu Met Asn Glu Thr Val Glu Val Ile Ser Glu Met Phe
 50                  55                  60
Asp Leu Gln Glu Pro Thr Cys Leu Gln Thr Arg Leu Glu Leu Tyr Lys
 65                  70                  75                  80
Gln Gly Leu Arg Gly Ser Leu Thr Lys Leu Lys Gly Pro Leu Thr Met
                 85                  90                  95
Met Ala Ser His Tyr Lys Gln His Cys Pro Pro Thr Pro Glu Thr Ser
                100                 105                 110
Cys Ala Thr Gln Ile Ile Thr Phe Glu Ser Phe Lys Glu Asn Leu Lys
             115                 120                 125
Asp Phe Leu Leu Val Ile Pro Phe Asp Cys Trp Glu Pro Val Gln Glu
 130                 135                 140
```

<210> SEQ ID NO 27
<211> LENGTH: 144
<212> TYPE: PRT
<213> ORGANISM: Homo sapiens

<400> SEQUENCE: 27

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Thr Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 28
<211> LENGTH: 144
<212> TYPE: PRT
<213> ORGANISM: Artificial
<220> FEATURE:
<223> OTHER INFORMATION: human GM-CSF with A117 mutation

<400> SEQUENCE: 28

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile

```
Met Trp Leu Gln Gly Leu Leu Leu Gly Thr Val Ala Cys Ser Ile
1               5                   10                  15

Ser Ala Pro Ala Arg Ser Pro Ser Pro Gly Thr Gln Pro Trp Glu His
            20                  25                  30

Val Asn Ala Ile Gln Glu Ala Arg Arg Leu Leu Asn Leu Ser Arg Asp
            35                  40                  45

Thr Ala Ala Glu Met Asn Lys Thr Val Glu Val Val Ser Glu Met Phe
        50                  55                  60

Asp Leu Gln Glu Pro Ser Cys Leu Gln Thr Arg Leu Glu Leu Tyr Lys
65                  70                  75                  80

Gln Gly Leu Gln Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Gln Ser Phe Lys Glu Asn Leu Lys
            115                 120                 125

Asp Phe Leu Leu Val Ile Pro Phe Asp Cys Trp Glu Pro Val Gln Glu
        130                 135                 140

<210> SEQ ID NO 30
<211> LENGTH: 144
<212> TYPE: PRT
<213> ORGANISM: Callithrix jacchus

<400> SEQUENCE: 30

Met Trp Leu Gln Asn Leu Leu Leu Gly Thr Val Ala Gly Ser Ile
1               5                   10                  15

Ser Ala Pro Thr His Leu Pro Ser Pro Asp Thr Gln Pro Ser Lys His
            20                  25                  30

Val Asn Ala Ile Gln Glu Ala Gln Arg Leu Leu Asn Leu Ser Arg Asp
            35                  40                  45

Thr Ala Pro Glu Thr Asn Glu Thr Val Glu Val Val Ser Glu Met Phe
        50                  55                  60

Asp Arg Gln Glu Pro Thr Cys Leu Gln Thr Arg Leu Glu Leu Tyr Lys
65                  70                  75                  80

Glu Ser Leu Trp Gly Ser Leu Thr Lys Leu Lys Gly Leu Leu Thr Met
                85                  90                  95

Ile Ala Ser His Tyr Lys Gln His Cys Pro Pro Thr Leu Glu Thr Ser
            100                 105                 110

Cys Ala Thr Lys Ile Ile Thr Phe Glu Ser Phe Lys Glu Asn Leu Lys
            115                 120                 125

Asp Phe Leu Leu Ala Ile Pro Val Asp Cys Trp Asp Pro Val Gln Glu
        130                 135                 140

<210> SEQ ID NO 31
<211> LENGTH: 336
<212> TYPE: DNA
<213> ORGANISM: Artificial
<220> FEATURE:
<223> OTHER INFORMATION: DNA encoding humanized 4K21 variable region
      light chain with H93Y mutation (4K21 hVL-H93Y)

<400> SEQUENCE: 31
gacatcgtga tgacccagtc ccccctgagc ctgcccgtga cccccggcga gcccgctagc      60
atcagctgcc ggtccagcca aagcttggtg aacagcaacg gcaacaccta cctgcactgg     120
tatctccaga agccaggaca gagcccccag ctgctgatct acaaggtctc caacaggttc     180
```

```
agcggcgtgc ccgaccggtt tagcggcagc ggctccggca ccgacttcac cctgaagatc        240
agccgggtgg aggccgagga cgtgggcgtg tactactgca gccagagcac ctacgtgccc        300
cccacctttg gcagggtac caaggtggag atcaag                                   336
```

<210> SEQ ID NO 32
<211> LENGTH: 336
<212> TYPE: DNA
<213> ORGANISM: Artificial
<220> FEATURE:
<223> OTHER INFORMATION: DNA encoding humanized 4K21 variable region
      light chain with S27eY, N28I, H34S, N53R, H93Y mutations (4K21
      hVL-S27eY-N28I-H34S-N53R-H93Y)

<400> SEQUENCE: 32

```
gacatcgtga tgacccagtc ccccctgagc ctgcccgtga cccccggcga gcccgctagc        60
atcagctgcc ggtccagcca aagcttggtg aactacatcg gcaacaccta cctgagctgg       120
tatctccaga agccaggaca gagccccag ctgctgatct acaaggtctc ccgcaggttc        180
agcggcgtgc ccgaccggtt tagcggcagc ggctccggca ccgacttcac cctgaagatc      240
agccgggtgg aggccgagga cgtgggcgtg tactactgca gccagagcac ctacgtgccc      300
cccacctttg gcagggtac caaggtggag atcaag                                 336
```

<210> SEQ ID NO 33
<211> LENGTH: 336
<212> TYPE: DNA
<213> ORGANISM: Artificial
<220> FEATURE:
<223> OTHER INFORMATION: DNA encoding humanized 4K21 variable region
      light chain with N28I, H34S, N53R, H93Y mutations
      (4K21 hVL-N28I-H34S-N53R-H93Y)

<400> SEQUENCE: 33

```
gacatcgtga tgacccagtc ccccctgagc ctgcccgtga cccccggcga gcccgctagc       60
atcagctgcc ggtccagcca aagcttggtg aacagcatcg gcaacaccta cctgagctgg     120
tatctccaga agccaggaca gagccccag ctgctgatct acaaggtctc ccgcaggttc      180
agcggcgtgc ccgaccggtt tagcggcagc ggctccggca ccgacttcac cctgaagatc     240
agccgggtgg aggccgagga cgtgggcgtg tactactgca gccagagcac ctacgtgccc     300
cccacctttg gcagggtac caaggtggag atcaag                                336
```

<210> SEQ ID NO 34
<211> LENGTH: 345
<212> TYPE: DNA
<213> ORGANISM: Artificial
<220> FEATURE:
<223> OTHER INFORMATION: DNA encoding murine 4K21 variable region heavy
      chain (4K21 mVH)

<400> SEQUENCE: 34

```
gaagtgcagc tggtggagtc tggggggaggc ttagtgaagt ctggagggtc cctgaaactc      60
tcctgtgcag cctctggatt cgctttcagt gcctatgaca tgtcttgggt tcgccagact     120
ccggagaaga ggctggaatt ggtcgcatac attagtagtg gtggtagtag tttttactat     180
ccagacactg tgaagggccg attcaccatc tccagagaca atgccaagaa caccctgtat     240
ctgcaaatga gcagtctgaa gtctgaggac acagccatgt attactgtac aagacatttg     300
gggtttgact actggggcca aggcaccact ctcacagtct cctca                     345
```

<210> SEQ ID NO 35

```
<211> LENGTH: 345
<212> TYPE: DNA
<213> ORGANISM: Artificial
<220> FEATURE:
<223> OTHER INFORMATION: DNA encoding humanized 4K21 variable region
      heavy chain (4K21 hVH)

<400> SEQUENCE: 35
gaggtgcagc tggtcgagag cggcggaggg ctggtgcagc caggcggcag cttgaggctg      60
tcctgcgccg ctagcggatt tgctttcagc gcctacgaca tgagctgggt gcggcaggcc     120
cctggcaagc gtctagaact ggtggcctac atcagcagcg gcggcagcag cttctactac     180
cccgacaccg tgaagggccg gttcaccatc agccgggaca cgccaagaa cagcctgtac      240 ctgcagatga acagcctgcg ggccgaggac accgccgtgt actactgcac ccggcacctg     300
ggcttcgact actggggcca gggtacccctg gtgaccgtga gcagc                    345

<210> SEQ ID NO 36
<211> LENGTH: 336
<212> TYPE: DNA
<213> ORGANISM: Artificial
<220> FEATURE:
<223> OTHER INFORMATION: DNA encoding murine 4K21 variable region light
      chain (4K21 mVL)

<400> SEQUENCE: 36
gacgtggtga tgacccagac cccctgagc ctgcccgtga gcctgggcga ccaggccagc       60
atcagctgca ggagcagcca gagcctggtg aacagcaacg gcaacaccta cctgcactgg    120
ttcctgcaga gccccggcca gagccccaag ctgctgatct acaaggtgag caacaggttc    180
agcggcgtgc ccgacaggtt cagcggcagc ggcagcggca ccgacttcac cctgaagatc    240
agcagggtgg aggccgagga cctgggcgtg tacttctgca gccagagcac ccacgtgccc    300
cccaccttcg gcggcggtac caagctggag atcaag                              336

<210> SEQ ID NO 37
<211> LENGTH: 336
<212> TYPE: DNA
<213> ORGANISM: Artificial
<220> FEATURE:
<223> OTHER INFORMATION: DNA encoding humanized 4K21 variable region
      light chain (4K21 hVL)

<400> SEQUENCE: 37
gacatcgtga tgacccagtc cccctgagc ctgcccgtga ccccggcga gcccgctagc        60 atcagctgcc ggtccagcca aagcttggtg aacagcaacg gcaacaccta cctgcactgg    120
tatctccaga agccaggaca gagcccccag ctgctgatct acaaggtctc caacaggttc    180
agcggcgtgc ccgaccggtt tagcggcagc ggctccggca ccgacttcac cctgaagatc    240
agccgggtgg aggccgagga cgtgggcgtg tactactgca gccagagcac ccacgtgccc    300
cccacctttg gccagggtac caaggtggag atcaag                              336

<210> SEQ ID NO 38
<211> LENGTH: 345
<212> TYPE: DNA
<213> ORGANISM: Artificial
<220> FEATURE:
<223> OTHER INFORMATION: DNA encoding humanized 4K21 variable region
      heavy chain with S55K, T62S mutations (4K21 hVH-S55K-T62S)

<400> SEQUENCE: 38
gaggtgcagc tggtcgagag cggcggaggg ctggtgcagc caggcggcag cttgaggctg      60
```

```
tcctgcgccg ctagcggatt tgctttcagc gcctacgaca tgagctgggt gcggcaggcc      120
cctggcaagc gtctagaact ggtggcctac atcagcagcg gcggcaagag cttctactac      180
cccgacagcg tgaagggccg gttcaccatc agccgggaca cgccaagaa cagcctgtac      240 ctgcagatga acagcctgcg ggccgaggac accgccgtgt actactgcac ccggcacctg      300
ggcttcgact actggggcca gggtaccctg gtgaccgtga gcagc                     345
```

```
<210> SEQ ID NO 39
<211> LENGTH: 345
<212> TYPE: DNA
<213> ORGANISM: Artificial
<220> FEATURE:
<223> OTHER INFORMATION: DNA encoding humanized 4K21 variable region
      heavy chain with S55R, T62S mutations (4K21 hVH-S55R-T62S)

<400> SEQUENCE: 39
```

```
gaggtgcagc tggtcgagag cggcggaggg ctggtgcagc caggcggcag cttgaggctg      60
tcctgcgccg ctagcggatt tgctttcagc gcctacgaca tgagctgggt gcggcaggcc      120
cctggcaagc gtctagaact ggtggcctac atcagcagcg gcggccgcag cttctactac      180
cccgacagcg tgaagggccg gttcaccatc agccgggaca cgccaagaa cagcctgtac      240 ctgcagatga acagcctgcg ggccgaggac accgccgtgt actactgcac ccggcacctg      300
ggcttcgact actggggcca gggtaccctg gtgaccgtga gcagc                     345
```

```
<210> SEQ ID NO 40
<211> LENGTH: 345
<212> TYPE: DNA
<213> ORGANISM: Artificial
<220> FEATURE:
<223> OTHER INFORMATION: DNA encoding humanized 4K21 variable region
      heavy chain with S56V, T62S mutations (4K21 hVH-S56V-T62S)

<400> SEQUENCE: 40
```

```
gaggtgcagc tggtcgagag cggcggaggg ctggtgcagc caggcggcag cttgaggctg      60
tcctgcgccg ctagcggatt tgctttcagc gcctacgaca tgagctgggt gcggcaggcc      120
cctggcaagc gtctagaact ggtggcctac atcagcagcg gcggcagcgt cttctactac      180
cccgacagcg tgaagggccg gttcaccatc agccgggaca cgccaagaa cagcctgtac      240 ctgcagatga acagcctgcg ggccgaggac accgccgtgt actactgcac ccggcacctg      300
ggcttcgact actggggcca gggtaccctg gtgaccgtga gcagc                     345
```

```
<210> SEQ ID NO 41
<211> LENGTH: 432
<212> TYPE: DNA
<213> ORGANISM: Homo sapiens
<220> FEATURE:
<221> NAME/KEY: misc_feature
<222> LOCATION: (1)..(432)
<223> OTHER INFORMATION: human GM-CSF cDNA ORF with I117 SNP

<400> SEQUENCE: 41
```

```
atgtggctgc agagcctgct gctcttgggc actgtggcct gcagcatctc tgcacccgcc      60
cgctcgccca gccccagcac gcagccctgg gagcatgtga atgccatcca ggaggcccgg      120
cgtctcctga acctgagtag agacactgct gctgagatga atgaaacagt agaagtcatc      180
tcagaaatgt ttgacctcca ggagccgacc tgcctacaga cccgcctgga gctgtacaag      240
cagggcctgc ggggcagcct caccaagctc aagggccct tgaccatgat ggccagccac      300
```

```
tacaagcagc actgccctcc aacccggaa acttcctgtg caacccagat tatcaccttt    360
gaaagtttca aagagaacct gaaggacttt ctgcttgtca tccctttga ctgctgggag    420 ccagtccagg ag                                                       432
```

<210> SEQ ID NO 42
<211> LENGTH: 432
<212> TYPE: DNA
<213> ORGANISM: Homo sapiens
<220> FEATURE:
<221> NAME/KEY: misc_feature
<222> LOCATION: (1)..(432)
<223> OTHER INFORMATION: human GM-CSF cDNA ORF with T117 SNP

<400> SEQUENCE: 42

```
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aacccggaa acttcctgtg caacccagac tatcaccttt    360
gaaagtttca aagagaacct gaaggacttt ctgcttgtca tcccctttga ctgctgggag    420
ccagtccagg ag                                                       432
```

<210> SEQ ID NO 43
<211> LENGTH: 452
<212> TYPE: DNA
<213> ORGANISM: Macaca mulatta
<220> FEATURE:
<221> NAME/KEY: misc_feature
<222> LOCATION: (1)..(452)
<223> OTHER INFORMATION: rhesus/cynomolgus monkey GM-CSF cDNA ORF

<400> SEQUENCE: 43

```
aggctaaagt tctctggagg atgtggctgc agggcctgct gctcttgggc actgtggcct     60
gcagcatctc tgcacccgcc cgctcaccca gccccggcac gcagccctgg gagcatgtga    120
atgccatcca ggaggcccgg cgtctcctga acctgagtag agacactgct gctgagatga    180
ataaaaccgt agaagtcgtc tcagaaatgt ttgacctcca ggagccgagc tgcctacaga    240
cccgcctgga gctgtacaag cagggcctgc agggcagcct caccaagctc aagggcccct    300
tgaccatgat ggccagccac tacaagcagc actgccctcc aacccggaa acttcctgtg    360 caacccagat tatcaccttc caaagtttca aagaaaacct gaaggacttt ctgcttgtca    420
tcccctttga ctgctgggag ccagtccagg ag                                 452
```

<210> SEQ ID NO 44
<211> LENGTH: 432
<212> TYPE: DNA
<213> ORGANISM: Callithrix jacchus
<220> FEATURE:
<221> NAME/KEY: misc_feature
<222> LOCATION: (1)..(432)
<223> OTHER INFORMATION: predicted marmoset GM-CSF cDNA

<400> SEQUENCE: 44

```
atgtggctgc agaacctgct gctcttgggc actgtggccg gcagcatctc tgcacctacc     60
cacttgccca gccccgacac acagccctcg aagcatgtga atgccatcca ggaggcccag    120
cgtctcctga acctgagtag agacactgct cctgagacaa atgaaacagt agaagtggtc    180
```

```
tcagaaatgt ttgaccgcca ggagccgacc tgcctacaga cccgcctgga gctgtacaag        240
gaaagcctgt ggggtagcct caccaagctc aagggactct tgaccatgat agccagccac        300
tacaagcagc actgccccccc aaccctggaa acttcctgtg caaccaagat tatcaccttt       360
gaaagtttca aagagaacct gaaggacttt ctgcttgcca tccctgttga ctgctgggat        420
ccagtccagg ag                                                            432
```

ANTIBODY WITH SPECIFICITY FOR GM-CSF (II)

CROSS-REFERENCE TO RELATED APPLICATIONS

This application is the U.S. National Phase Application of PCT/EP2011/070375, filed Nov. 17, 2011, which claims priority to EP 10191664.1, filed Nov. 18, 2010, the contents of each are hereby incorporated by reference in their entireties.

The present invention relates to antibodies with specificity for granulocyte-macrophage colony stimulating factor (GM-CSF). More particularly, the invention relates to humanized monoclonal antibodies that bind specifically to human GM-CSF with high affinity. The invention also relates to nucleic acids encoding the antibodies, vectors for expression of these nucleic acids, and host cells for producing said antibodies. Further, the invention relates to the use of said antibodies in the diagnosis or treatment of autoimmune or inflammatory diseases.

Granulocyte-macrophage colony stimulating factor (GM-CSF) is a hematopoietic cytokine that stimulates the differentiation of progenitor cells into monocytes and granulocytes (eosinophils, neutrophils, and basophils). GM-CSF is mainly produced from activated T cells, macrophages and endothelial cells, but secretion of this cytokine has been observed from a plethora of cells and cell lines.

GM-CSF is also a potent. inflammatory cytokine, whose activity or overexpression can have significant detrimental effects. It is implicated in a variety of autoimmune and inflammatory diseases including rheumatoid arthritis, asthma, multiple sclerosis and idiopathic thrombocytopenic purpura. For example, it has been reported that GM-CSF$^{-/-}$ mice develop no disease in a collagen-induced arthritis model. Further, in asthma and rheumatoid arthritis, elevated levels of GM-CSF have been detected and correlated with the inflammatory process.

Neutralization or blockage of GM-CSF activity is therefore a promising approach in the treatment and/or prevention of autoimmune or inflammatory conditions. In particular, GM-CSF neutralization or blockage may be achieved by antibodies directed to GM-CSF. In order to neutralize GM-CSF, or be neutralizing, binding of an antibody partially or completely inhibits one or more biological activities of GM-CSF. For example, the antibody reduces inflammatory responses mediated by GM-CSF.

WO 2008/141391 discloses antibodies that bind to GM-CSF or fragments thereof and antagonize or neutralize GM-CSF activity. The content of this document is herein incorporated by reference. In particular, this document refers to a humanized form of murine monoclonal antibody 4K21 deposited on 17 May 2007 at the European Collection of Cell Cultures (ECACC), Centre for Applied Microbiology and Research, Porton Down, Salisbury, United Kingdom, under Accession No. 07051601.

The genomic sequence encoding the epitope recognized by this antibody contains a single nucleotide polymorphism (SNP), leading to two diverse codons coding for isoleucine (I) and threonine (T), respectively, at position 117 of human GM-CSF protein (see FIG. 1a)). These alleles are differentially distributed within the human population. According to the HapMap data in the GenBank SNP database, the European population is composed by 80% of the I117 allele, whereas the T117 allele is predominant in the Asian population by 60%. The resulting proportion of the dominant isoform in homozygotes is 62% I117 for European and 42% T117 for Asians, the rest being mostly heterozygotes in both populations.

Experimental data have shown that the anti-GM-CSF 4K21 recombinant chimeric and humanized molecules, e.g. clone hGM4/34 of WO 2008/141391, have a preference for the human GM-CSF I117 target protein, with a ≥9 fold lower affinity for the T117 target protein in solution as determined by $K_d$ measurements. Likewise, these antibodies show lower potency ($IC_{50}$ of GM-CSF dependent TF-1 cell proliferation and IL-8 secretion in U937 cells) for the T117 containing GM-CSF protein.

GM-CSF protein is highly conserved among different species of the order Primates, e.g. man, macaca and marmoset (FIG. 1b)). It was shown that 4K21 antibodies had a significant difference in affinity and potency between the human I117 protein and the macaca ortholog, which is at the limit of acceptability for preclinical studies, as well as no neutralization potential towards marmoset GM-CSF. Further, a surface-exposed deamidation site, NS<u>N</u>GNT, is present in the complementarity determining region (CDR)1 of the variable light chain region, which could lead to a heterogenic product and affect affinity and potency of the antibody.

Accordingly, there was a need for anti-GM-CSF antibodies with improved properties. It was an object of the present invention to provide antibodies with specificity to human GM-CSF to overcome the problems of state-of-the-art-antibodies such as 4K21. In particular, the newly developed antibodies should have improved potency to both GM-CSF protein isoforms as well as improved cross-reactivity to the macaca ortholog, better affinity maturation and biochemical properties, such as Fab stability. Preferably, the newly developed antibodies are based on 4K21.

Surprisingly, it could be shown that mutation of a single amino acid, histidine at position 93 in the variable light chain region of the humanized 4K21 antibody, significantly improved the properties of the resulting antibody.

A first aspect of the invention therefore relates to an antibody that binds to human GM-CSF, which comprises
(i) a heavy chain variable region comprising complementarity determining regions CDR1, CDR2, and CDR3 as shown in SEQ ID NOs: 1, 2, and 3, or variants thereof wherein optionally 1, 2, or 3 amino acids in each CDR may be substituted by different amino acids; and
(ii) a light chain variable region comprising complementarity determining regions CDR1, CDR2; and CDR3 as shown in SEQ ID NOs: 4, 5 and 6, or variants thereof wherein optionally 1, 2, or 3 amino acids in each CDR may be substituted by different amino acids, with the proviso that the amino acid tyrosine at position 93 in the light chain CDR3 as set forth in SEQ ID NO:6 is not substituted, or an antigen-binding fragment thereof.

Examples for "human GM-CSF" are the naturally occurring I117-(SEQ ID NO: 26) and T117-(SEQ ID NO: 27) isoforms, as well as further naturally occurring isoforms and artificially produced mutants. Such mutants may carry one, two, three, four, five, ten or more amino acid substitutions, deletions, and/or insertions, as long as the biological activity of the protein is retained. One example for a GM-CSF mutant carrying a single amino acid substitution is set forth in SEQ ID NO: 28 (A117).

The term "antibody" as used in the present invention comprises all the various forms of antibodies including, but not limited to whole antibodies and antigen-binding fragments thereof, e.g. Fv, Fab, Fab' and F(ab')2, diabodies, minibodies, domain antibodies (dAb), camelid antibodies (IgG) and nanobodies (VHH), monovalent antibodies, divalent or multivalent antibodies comprising a fragment of more than one antibody, single chain variable fragments (scFv), and antibody derivatives such as immunoglobulin-derived polypeptides, disulfide stabilized Fv fragments (dsFv), CDR-comprising peptides etc. Antibody fragments such as Fabs (approx. 60 kDa) or scFvs (about 20-30 kDa) and still smaller fragments of antibodies are of great interest and advantageous for pharmaceutical applications or as imaging agents.

Preferably, the antibody comprises at least one heavy immunoglobulin chain and at least one light immunoglobulin chain, for example two heavy chains and two light chains, which may be covalently linked via disulfide bonds. A functional structure analogous to the isotype G of immunoglobulins (IgG) is preferred. Among these, antibodies of the IgG1-, IgG2-, IgG3-, or IgG4-type are preferred. However, the antibody or antigen-binding fragment thereof according to the invention may also be of the IgA-, IgD-, IgE-, or IgM-type, preferably of the IgM1- and IgM2-type.

An immunoglobulin chain comprises a variable domain and optionally a constant domain. A variable domain (also referred to as variable region) comprises complementarity determining regions (CDRs), e.g. a CDR1, CDR2 and/or CDR3 region, and framework regions (FRs). The term "complementarity determining region" (CDR) is well-defined in the art (see, for example, Harlow and Lane (eds.), Antibodies: A Laboratory Manual, CSHL Press, Cold Spring Harbor, N.Y., 1988; incorporated herein by reference in its entirety) and refers to the stretches of amino acids within the variable domain of an antibody that primarily make contact with the antigen and determine antibody specificity. The antibodies of the invention have at least one antigen binding site, e.g. one or two antigen binding sites. In certain embodiments, e.g. for CDR-comprising peptides, a variable domain may contain only CDRs linked via short linker peptides instead of complete framework regions.

The term "bind" or "binding" of an antibody means an at least temporary interaction or association with or to a target antigen, e.g. GM-CSF, comprising fragments thereof containing an epitope.

The antibody according to the invention binds to GM-CSF or a fragment thereof. Typically, antibodies show species-specificity for GM-CSF. In the present invention, high specificity for human GM-CSF is preferred. However, depending on the degree of sequence identity between GM-CSF homologs of different species, a given antibody or antigen-binding fragment may show cross-reactivity with GM-CSF from at least one other species, e.g. macaca, marmoset, dog, rabbit, mouse and/or rat. For antibodies directed towards human GM-CSF, some level of cross-reactivity with other mammalian forms of GM-CSF may be desirable in certain circumstances, for example when testing antibodies in animal models of a particular disease or for conducting toxicology, safety and dosage studies.

The antibody according to the invention comprises a variable heavy chain region (VH) and/or a variable light chain region (VL), whose CDRs show a high degree of sequence identity to murine and/or humanized 4K21 complementarity determining region sequences (VH: SEQ ID NOs: 1, 2, 3; VL: SEQ ID NOs: 4, 5, 6). In the VL CDR3 sequence, the amino acid tyrosine is substituted for histidine. According to the numbering of Kabat et al. (Sequences of Proteins of Immunological Interest, US Dept. Health and Human Services, NIH Publication No. 91-3242 (1991); incorporated herein by reference), which is used throughout this invention, this histidine is assigned position number 93; the substitution is therefore referred to as VL H93Y. The VL CDR3 is shown in SEQ ID NO:6 with the H9 3Y substitution, and in SEQ ID NO:7 without the substitution.

Besides the H93Y substitution in the variable light chain region and murine back mutations introduced during humanization (see below), which are also encompassed by the present invention, antibodies or fragments thereof according to the invention may contain one or more, e.g. 2, 3, 4, 5, 6, 7, 10, 15 and up to 18 additional mutations. These polypeptide chains are encompassed by the term "variants".

The term "mutation" or "mutated" as used in the context of the present invention includes the deletion, insertion and substitution of amino acids and/or nucleotides. Substitutions are preferred, but deletions and/or insertions are also possible, as long as binding of the resulting antibody to GM-CSF is not abolished.

It is contemplated that the framework regions flanking the CDRs may be entirely or partially substituted. However, it is preferred that the degree of sequence identity of the VL and/or VH regions according to the invention to those of the murine and/or humanized 4K21 is at least 70%, preferably at least 80%, more preferably at least 90%, and most preferably at least 95%. In preferred embodiments, the antibody comprises a variable light chain region sequence selected from the group consisting of SEQ ID NOs: 8, 9 and 10.

The percentage "sequence identity" of two sequences may be determined using the BLASTP algorithm (Altschul et al., Gapped BLAST and PSI-BLAST: a new generation of protein database search programs, Nucleic Acids Res. 25:3389-3402, 1997; incorporated herein by reference) using default parameters.

Additional mutations are preferably located in the CDRs of both the heavy and the light chain. In particular, 1, 2, or 3 amino acids in each heavy and/or light chain CDR may be mutated. In preferred embodiments, at least one of the amino acids serine at position 55 (VH S55), serine at position 56 (VH S56), threonine at position 62 (VH T62) in the heavy chain CDR2, and/or asparagine at position 28 (VL N28), histidine at position 34 (VL H34) in the light chain CDR1, and/or asparagine at position 53 (VL N53) in the light chain CDR2 can be substituted by another amino acid. Optionally also the serine at position 27e (VL S27e) of the light chain CDR1 may be substituted by another amino acid.

Still more preferably, one or more specific amino acids may be substituted for one or more of the above-indicated amino acids. Accordingly, in especially preferred embodiments of the invention, VH S55 is substituted by lysine or arginine (VH S55K or VH S55R), and/or VH S56 is substituted by valine (VH S56V), and/or VH T62 is substituted by serine (VH T62S), and/or VL H34 is substituted by serine (VL H34S), and/or VL N28 is substituted by isoleucine (VL N28I), and/or VL N53 is substituted by arginine (VL N53R). In a further embodiment, the amino acid tyrosine is substituted for the serine at position 27 of the light chain CDR1 (VL S27eY).

Still more preferably, the antibody according to the invention comprises a variable heavy chain region comprising complementarity determining regions CDR1 as shown in SEQ ID NO:1, CDR2 selected from SEQ ID NOs: 11, 12, and 13, and CDR3 as shown in SEQ ID NO:3, and a variable light chain region comprising complementarity determining regions CDR1 selected from SEQ ID NOs: 14 and 15, CDR2 as shown in SEQ ID NO: 16, and CDR3 as shown in SEQ ID NO:6.

In a preferred embodiment, the affinity of the antibody of the invention to the human GM-CSF T117 and I117 alleles differs by a factor of less than 5, preferably less than 2. This means that the strength of binding of the antibody to human GM-CSF does not depend on the amino acid at position 117. The affinity of an antibody is defined as the monovalent binding strength of one molecule to another, e.g. one epitope to one paratope. The value of the antibody affinity can be expressed as an equilibrium constant K, e.g. the equilibrium dissociation constant, $K_d$ which is defined as $k_{off}/k_{on}$, i.e. the ratio of the reverse rate constant ($k_{off}$) to the forward rate constant ($k_{on}$). The $K_d$ values are given in mol/l or M. The affinity can be determined e.g. via measurement of binding constants and calculation of $K_d$ using a kinetic exclusion assay (KINEXA® system, Sapidyne Instruments, Inc.).

In a further preferred embodiment, the potency of the antibody according to the invention to the human GM-CSF T117 and I117 alleles differs by a factor of less than 5, preferably less than 2. This means that the antibody can be used to neutralize both isoforms of human GM-CSF to a similar extent. The potency may be expressed as the concentration of antibody/antigen-binding fragment which produces the half-maximal effect at a given antigen concentration. For example, the "effect" of an antibody may be inhibition or neutralization of an antigen. In this case, the antibody concentration producing the half-maximal inhibition may be referred to as $IC_{50}$, which is given in mol/l or M. Potency is usually influenced by affinity until, at a given antigen concentration, an affinity is reached beyond which further improvements in affinity will not enhance binding of the antigen anymore (so-called potency ceiling). Potency may for example be determined by measuring the $IC_{50}$ values of GM-CSF dependent TF-1 cell proliferation and/or of GM-CSF dependent IL-8 secretion in U937 cells.

In yet a further preferred embodiment, the antibody is a monoclonal antibody, a chimeric antibody, a recombinant antibody and/or a human or humanized antibody. A monoclonal antibody (also referred to as mAB) is a single molecular species of antibody and is usually produced by creating hybrid antibody-forming cells from a fusion of nonsecreting myeloma cells with immune spleen cells. Polyclonal antibodies, by contrast, are produced by injecting an animal (such as a rodent, rabbit or goat) with an antigen, and extracting serum from the animal. A chimeric antibody is an antibody in which the variable domain of e.g. a murine antibody is combined with the constant region of a human antibody. Recombinant antibodies are obtained via genetic engineering without having to inject animals. Human antibodies according to the invention may be prepared using transgenic mice or by phage display; these methods are well known in the art.

A humanized antibody is a genetically engineered (monoclonal) antibody in which the CDRs from a donor antibody, e.g. an antibody from mouse, rat, hamster etc. are grafted onto an acceptor antibody, i.e. a human antibody. Typically, a humanized antibody comprises a light chain comprising three CDRs from a murine antibody, a variable domain framework from a human antibody, and a human constant region, and a heavy chain comprising three CDRs from a murine antibody, a variable domain framework from a human antibody, and a human constant region. Humanization of antibodies may be performed to avoid an immune response, resulting in generation of human anti-mouse antibodies (HAMA), the so-called HAMA response. Methods for the humanization of antibodies, e.g. CDR grafting, are well known in the art. In the context of the present invention, humanized monoclonal antibodies are particularly preferred.

Preferred examples of antibodies according to the invention are based on humanized 4K21 variable region heavy chain (4K21 hVH; SEQ ID NO: 18) and the corresponding light chain 4K21-hVL carrying the H93Y mutation (SEQ ID NO: 8). Exemplary heavy chains based on humanized 4K21 with preferred mutations are 4K21 hVH-S55K-T62S (SEQ ID NO: 21), 4K21 hVH-S55R-T62S (SEQ ID NO: 22), and 4K21 hVH-S56V-T62S (SEQ ID NO: 23). Exemplary light chains based on humanized 4K21 with preferred mutations are 4K21 hVL-S27eY-N28I-H34S-N53R-H93Y (SEQ ID NO: 9) and 4K21 hVL-N28I-H34S-N53R-H93Y (SEQ ID NO: 10).

The antibody according to the invention may be glycosylated. Typically, monosaccharaides such as N-acetylglucosamine, mannose, glucose, galactose, fucose, sialic acid etc. are assembled to oligosaccharides at individual glycosylation sites. The glycosylation pattern may be the same as or different from the pattern found in a host species, e.g. mouse, macaca, marmoset, or man.

It is also contemplated that the antibody according to the invention may be conjugated with a further molecule. The further molecule may be conjugated to the antibody directly or via a spacer of suitable length. For therapeutic purposes, conjugation with a therapeutic effector group, such as a radioactive group, i.e. a group consisting of or comprising a radioisotope or radionuclide (e.g. $^{3}H$, $^{14}C$, $^{15}N$, $^{33}P$, $^{35}S$, $^{90}Y$, $^{99}Tc$, $^{111}In$, $^{123}I$, $^{125}I$, $^{131}I$, $^{201}Tl$, $^{213}Bi$), a toxin, or a cytotoxic group, e.g. a cell growth inhibitor may be suitable. In another aspect, the antibody or antigen-binding fragment thereof can be coupled to a labeling group (labeled antibody), which may then be used e.g. for diagnostic purposes. Suitable labeling groups may be selected from radioisotopes (e.g. those mentioned supra) or groups containing a radioisotope, radionuclides, fluorescent groups (e.g. fluorescent proteins such as GFP, RFP etc., Alexa-Fluor® dyes, rhodamines, fluorescein and its derivatives such as FITC, cyanine dyes such as Cy3® and Cy5®, enzymatic groups (e.g. horseradish peroxidase, alkaline phosphatase, β-galactosidase), chemiluminescent groups, biotinyl groups, metal particles, (e.g. gold particles), magnetic particles (e.g. with a core containing magnetite ($Fe_3O_4$) and/or maghemite ($Fe_2O_3$)), predetermined polypeptide groups, etc.

In another aspect, the invention relates to a nucleic acid, preferably an isolated nucleic acid, encoding the antibody of the invention. The nucleic acid of the invention encoding the above-described antibody or antigen-binding fragment may be, e.g., a natural DNA or RNA or a recombinantly or synthetically produced DNA, RNA or LNA or a recombinantly produced chimeric nucleic acid molecule comprising any of these nucleic acids either alone or in combination. The nucleic acid may also be genomic DNA corresponding to an entire gene or a substantial portion thereof or to fragments and derivatives thereof. The nucleotide sequence may correspond to the naturally occurring nucleotide sequence or may contain single or multiple nucleotide substitutions, deletions or additions. The nucleic acid may also be fused to another nucleic acid. In a particularly preferred embodiment of the present invention, the nucleic acid is a cDNA molecule.

The nucleic acid according to the invention is preferably selected from
(i) one or more nucleic acid sequences set forth in SEQ ID NOs. 31-40, with SEQ ID NOs. 31-35 and 38-40 being particularly preferred,
(ii) nucleic acid sequences comprising sections encoding CDRs as set forth in SEQ id NOs: 1-6 and 11-16,
(iii) nucleic acid sequences encoding a polypeptide selected from the group consisting of SEQ ID NOs: 8-10, 17-18, and 21-23.

(iv) nucleic acid sequences complementary to any of the sequences in (i), (ii) or (iii), and (v) nucleic acid sequences capable of hybridizing to (i), (ii), (iii) or (iv) under stringent conditions and encoding a polypeptide, wherein an antibody or functional fragment thereof comprising said polypeptide binds to GM-CSF.

The term "stringent conditions" is readily understood by the skilled person and may refer, e.g., to hybridization in 6.0×SSC at about 45° C. followed by a washing step with 2.0×SSC at 50° C. (see e.g. Sambrook et al., Molecular Cloning: A Laboratory Manual, 3rd ed., CSHL Press, Cold Spring Harbor, N.Y., 2001; incorporated herein by reference in its entirety).

The invention also relates to a vector or vector system comprising a nucleic acid of the invention. A vector according to the invention may be, for example, a plasmid, a phage, a phagemid, a viral or a retroviral vector. Retroviral vectors may be replication competent or replication defective. In the latter case, viral propagation generally will occur only in complementing host cells. A vector system according to the invention comprises a vector as defined supra and optionally further vectors which may be required for the respective application.

In a preferred embodiment, the vector or vector system comprises an expression vector. An expression vector is generally used to introduce a specific gene into a target cell in order to express it, usually to produce high quantities of nucleic acids or proteins encoded by said gene, and typically contains an origin of replication, expression control sequences as well as specific genes capable of providing phenotypic selection of the transformed cells.

In an expression vector, the nucleic acid of the invention is operably linked to one or more expression control sequences allowing the transcription and optionally translation in prokaryotic and/or eukaryotic host cells. The term "operably linked" means that a nucleic acid sequence is placed into a functional relationship with another nucleic acid sequence. The expression control sequences define, inter alia, the location at which the RNA polymerase binds and at which the ribosomes bind and interact with the mRNA (the product of transcription) to initiate translation of the mRNA into protein. The expression control sequence may be constitutively or regulatably active. Suitable expression control sequences include prokaryotic promoter sequences, e.g. lac, trp, tac, T7, araB or phoA promoters, eukaryotic promoter sequences, e.g. ADH1, AOX, CYC1, GAL1, or PGK1 promoters in yeast or the CMV-, SV40-, RSV and other promoters in higher eukaryotic cells, operator sequences such as lacO or tetO, enhancer sequences, e.g. CMV- or SV40-enhancer, and terminator sequences.

Besides elements which are responsible for the initiation of transcription, expression control sequences may also comprise transcription termination signals, such as the SV40-poly-A site or the tk-poly-A site, located downstream of the nucleic acid sequence of interest. Additional expression control sequences may include translational enhancers. In general, vectors containing expression control sequences which facilitate the efficient transcription and/or translation of the inserted nucleic acid molecule are chosen in accordance with the respective host.

Suitable expression vectors advantageously contain elements enabling selection in the host cell. For example, the vector comprising a nucleic acid of the invention may contain at least one selectable marker, e.g. an antibiotic resistance marker or an auxotrophic marker.

Methods to construct the vectors according to the invention and to introduce them into suitable hosts or host cells, e.g. by (co)transformation, (co)transfection, or (co)infection, are well known to those skilled in the art (see e.g. Sambrook et al., 2001, supra).

The invention further relates to a non-human host organism or a host cell for expressing the nucleic acids according to the invention. The nucleic acid or vector of the invention, which is present in the host, may either be integrated into the genome of the host or host cell or it may be maintained extrachromosomally.

Suitable non-human hosts include all bacterial species which can be transformed or transfected with a nucleic acid sequence for its expression, for example *Escherichia coli, Salmonella typhimurium, Serratia marcescens* and *Bacillus subtilis*. Preferred fungal hosts are, inter alia, of the family Saccharomycetaceae, e.g. *Saccharomyces cerevisiae, Hansenula* polymorphs or *Pichia pastoris*. Among mammalian hosts, goats, cows, horses, pigs, rats, mice, rabbits, hamsters and chicken are preferred. There, antibodies can be produced in and recovered from tissue or body fluids, such as milk, blood or urine.

The host cell can be any prokaryotic or eukaryotic cell, such as a bacterial, fungal, plant, or animal cell. Suitable prokaryotic cells include cells of bacterial species as described above. Likewise, preferred fungal cells are those of Saccharomycetaceae species as described above. Preferred animal cells include but are not limited to, insect, amphibian, mammalian or, more preferably, human cells. Suitable insect cells are e.g. cells of the SF9 cell lines. Preferred mammalian cells include Chinese hamster ovary cells (CHO, ATCC CCL-61), baby hamster kidney (BHK) cells, monkey kidney cells (COS, ATCC CRL-1650), 3T3 cells or NIH3T3 cells derived from a mouse fibroblast (ATCC No. CRL-1658), NSO cells and a number of other cell lines. Suitable human cells include, but are not limited to human embryonic kidney cells (HEK293, 293T), Hela cells, human hepatocellular carcinoma cells (e.g., Hep G2), and A549 cells.

According to another embodiment of the invention, antibodies or antigen-binding fragments thereof are produced by cell lines. These cell lines may be hybridomas, i.e. hybrid cell lines obtained by fusing a specific antibody-producing B lymphocyte with a myeloma cell and appropriate selection, which is well known in the art. Also contemplated are cell lines, e.g. 293 or CHO cell lines, transformed with a vector or vector system as described supra.

Methods for preparing fused and/or operably linked genes and expressing them in bacteria or animal cells are well-known in the art (Sambrook et al., 2001, supra). The genetic constructs and methods described therein can be utilized for expression of antibodies according to the invention in, e.g., prokaryotic hosts. The nucleic acid sequences encoding individual polypeptide chains of an antibody may be expressed from a single vector or co-expressed from two or more distinct vectors. For example, one vector may encode an IgG heavy chain, and the other may encode a light chain. The transformed prokaryotic hosts or transfected higher eukaryotic host cells may be cultured according to techniques known in the art to achieve optimal cell growth. The antibodies or antigen-binding fragments thereof can then be isolated from the growth medium, cellular lysates, or cellular membrane fractions. The isolation and purification of the microbially or otherwise expressed antibodies or antigen-binding fragments thereof can be performed with conventional means such as preparative chromatographic separations, immunological separations, etc.

The present invention further relates to a pharmaceutical composition comprising an antibody or antigen-binding fragment thereof. It is also possible that the pharmaceutical composition comprises a nucleic acid encoding said antibody or antigen-binding fragment thereof, a vector or vector system containing said nucleic acid and/or a preferably human cell producing said antibody or antigen-binding fragment thereof. Optionally, the pharmaceutical composition comprises pharmaceutically acceptable excipients, adjuvants and/or carriers.

As exemplary excipients, disintegrators, binders, fillers, and lubricants may be mentioned. Examples of disintegrators include agar-agar, algins, calcium carbonate, cellulose, colloid silicon dioxide, gums, magnesium aluminium silicate, methylcellulose, and starch. Examples of binders include microcrystalline cellulose, hydroxymethyl cellulose, hydroxypropylcellulose, and polyvinylpyrrolidone. Examples of fillers include calcium carbonate, calcium phosphate, tribasic calcium sulfate, calcium carboxymethylcellulose, cellulose, dextrin, dextrose, fructose, lactitol, lactose, magnesium carbonate, magnesium oxide, maltitol, maltodextrins, maltose, sorbitol, starch, sucrose, sugar, and xylitol. Examples of lubricants include agar, ethyl oleate, ethyl laureate, glycerin, glyceryl palmitostearate, hydrogenated vegetable oil, magnesium oxide, stearates, mannitol, poloxamer, glycols, sodium benzoate, sodium lauryl sulfate, sodium stearyl, sorbitol, and talc.

Usual stabilizers, preservatives, wetting and emulsifying agents, consistency-improving agents, flavour-improving agents, salts for varying the osmotic pressure, buffer substances, solubilizers, diluents, emollients, colorants and masking agents and antioxidants come into consideration as pharmaceutical adjuvants.

Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting-point wax, cocoa butter, water, alcohols, polyols, glycerol, vegetable oils and the like.

The pharmaceutical composition may also comprise at least one further active agent, e.g. one or more further antibodies or antigen-binding fragments thereof, peptides, proteins, nucleic acids, organic and inorganic molecules.

In a preferred embodiment of the invention, the pharmaceutical compositions comprising an antibody or antigen-binding fragment thereof are for use in medicine or diagnostics. Preferably, the pharmaceutical compositions are for use in human medicine, but they may also be used for veterinary purposes.

In particular, the antibodies or antigen-binding fragments thereof, the nucleic acids, the vector or vector system, the host or host cell of the invention, or a pharmaceutical composition comprising an antibody or antigen-binding fragment thereof are for use in the diagnosis, prevention or treatment of disorders associated with, caused by or accompanied by elevated levels and/or activity of GM-CSF, and other diseases or conditions which may be beneficially diagnosed, prevented, or treated by inhibiting and/or neutralizing GM-CSF activity via the administration of antibodies or antigen-binding fragments thereof as described supra.

In a further embodiment, the present invention relates to methods for the diagnosis, prevention or treatment of disorders associated with, caused by or accompanied by elevated levels and/or activity of GM-CSF, and other diseases or conditions which may be beneficially diagnosed, prevented, or treated by inhibiting and/or neutralizing GM-CSF activity.

Preferred medical indications are autoimmune or inflammatory diseases or conditions associated with elevated levels and/or activity of GM-CSF. The disease or condition may be selected from, for example, asthma, rheumatoid arthritis, chronic obstructive pulmonary disease, idiopathic thrombocytopenic purpura, acute respiratory distress syndrome, multiple sclerosis, Alzheimer's disease, Crohn's disease, irritable bowel syndrome, colitis, psoriasis, macular degeneration, uveitis, Wallerian degeneration, antiphospholipid syndrome, restinosis, atherosclerosis, idiopathic pulmonary fibrosis, relapsing polychondritis, hepatitis, glomerulonephritis, nephritis, lupus, atopic dermatitis, sarcoidosis, osteoarthritis, osteoporosis and osteolytic tumors, the treatment of bone metastasis in myeloma, prostate or breast cancer, or, alternatively, prevention of the formation of breast cancer metastasis, leukemia and other metabolic diseases. Particularly preferred indications are rheumatoid arthritis, multiple sclerosis, asthma and chronic obstructive pulmonary disease.

An antibody or antigen-binding fragment thereof or a pharmaceutical composition according to the invention can be administered to a subject in need thereof in an amount effective to obtain the desired therapeutic or prophylactic effect. For example, one desired effect to be achieved by said administration may be to block, inhibit and/or neutralize one or more biological function(s) of GM-CSF. In this context, administration may comprise contacting the antibody of the invention with cells or a tissue suspected of expressing GM-CSF, preferably at high and/or aberrant levels, under conditions, wherein the antibody is capable of blocking, inhibiting and/or neutralizing GM-CSF function. The contacting may be in vitro or in vivo.

Administration of suitable compositions may be effected in different ways, e.g., by intravenous, intraperitoneal, subcutaneous, intramuscular, topical, oral, intradermal, intranasal or intrabronchial administration. Administration may also be conducted directly at the target site.

The dosage regimen will be determined by the attending physician and clinical factors. As is well known in the medical arts, dosage for any one patient depends upon many factors, including the patient's size, weight, body surface area, age, the particular compound to be administered, the activity of the employed antibody or antibodies, time and route of administration, general health, and combination with other therapies or treatments. Proteinaceous pharmaceutically active matter may be present in amounts between 1 µg and 100 mg/kg body weight per dose; however, doses below or above this exemplary range are also envisioned. If the regimen is a continuous infusion, it may be in the range of 1 pg to 100 mg per kilogram of body weight per minute.

A neutralizing antibody or antigen-binding fragment thereof according to the invention may be employed at a concentration of, e.g., 0.01, 0.1, 0.5, 1, 2, 5, 10, 20 or 50 µg/ml in order to inhibit and/or neutralize a biological function of GM-CSF by at least about 50%, preferably 75%, more preferably 90%, 95% or up to 99%, and most preferably approximately 100% (essentially completely) as assayed by methods well known in the art.

According to further aspects of the invention, the antibodies and antigen-binding fragments thereof may be used additional applications in vivo and in vitro. For example, antibodies or antigen-binding fragments of the invention may be employed for diagnostic purposes, e.g. in assays designed to detect and/or quantify the presence of GM-CSF and/or to purify GM-CSF. Antibodies may also be tested in animal models of particular diseases and for conducting toxicology, safety and dosage studies.

Finally, the invention relates to a kit comprising at least one antibody or antigen-binding fragment thereof according to the invention, at least one nucleic acid sequence encoding said components, the vector or vector system of the invention, and/or a host cell according to the invention. It is contemplated that the kit may be offered in different forms, e.g. as a diagnostic kit.

The present invention shall be further illustrated by the following Figures and Examples.

BRIEF DESCRIPTION OF THE FIGURES

FIG. 1: a) Alignment of human GM-CSF protein sequences: A single nucleotide polymorphism (SNP) leads to substitution of the amino acid threonine (GM-CSF I117; SEQ ID NO:26) for isoleucine (GM-CSF T117; SEQ ID NO:27).

b) Alignment of human (SEQ ID NO:26), macaca (SEQ ID NO:29), and the predicted marmoset (SEQ ID NO: 30) GM-CSF protein sequences. Bottom paragraph gives scores of pairwise alignment.

FIG. 2: Alignment of the murine and humanized 4K21 variable region sequences with human VH3 (V-base VH3-07, i.e. IGHV3-7; SEQ ID NO:24) and VK2 (V-base VK2-A3, i.e. IGKV2-28; SEQ ID NO:25) germ line genes. 4K21-mVH (SEQ ID NO:17) and -hVH (SEQ ID NO:18), mVL (SEQ ID NO:19) and hVL (SEQ ID NO:20). Back mutations are shown in bold, investigated CDR positions in italics. Underlined residues indicate preferred embodiments of the invention. Numbering and CDR limits are as described in Kabat et al.: Sequences of Proteins of Immunological Interest, US Dept. Health and Human Services, NIH Publication No. 91-3242 (1991).

Figure 3A:
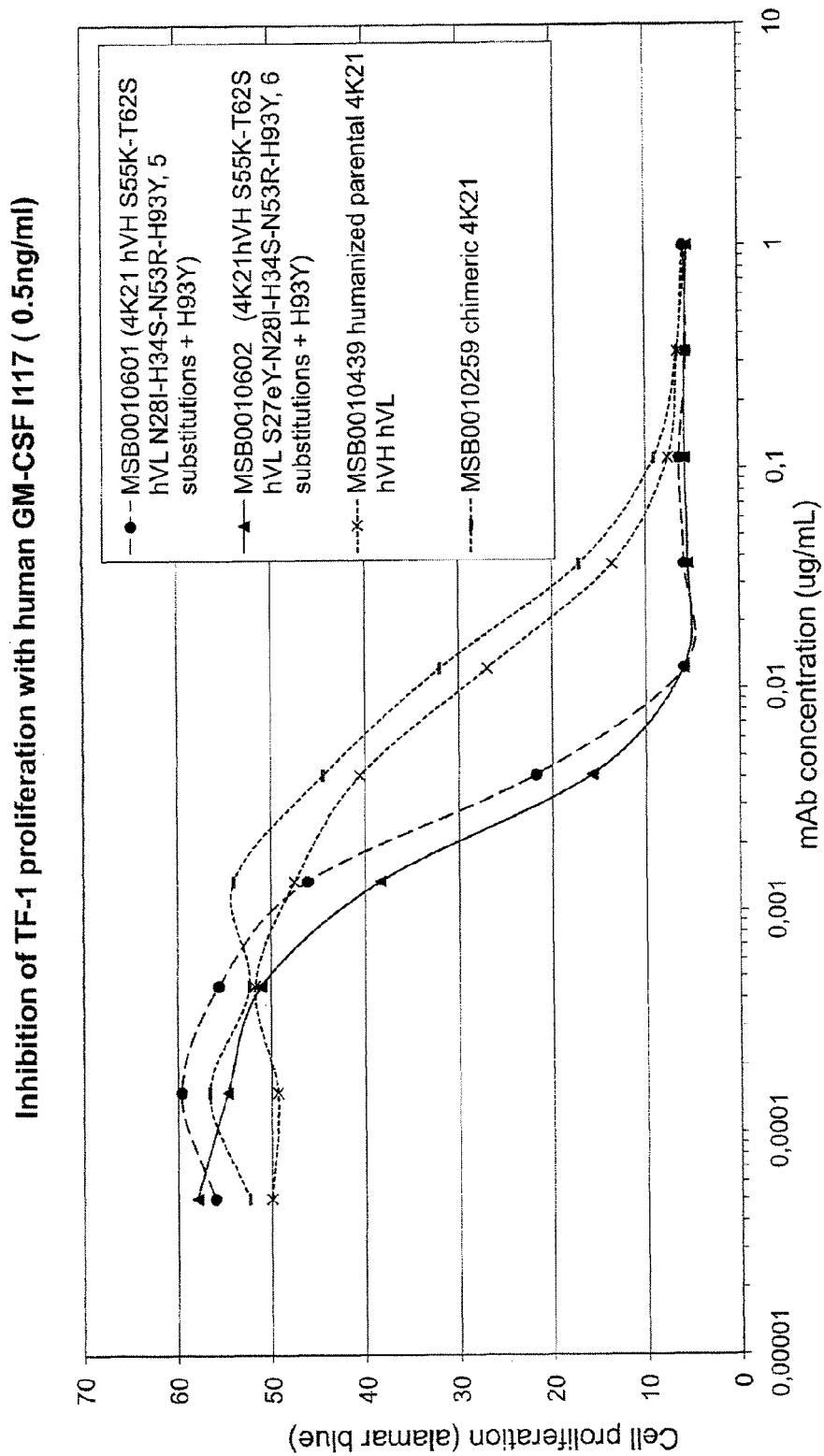
Figure 3B:
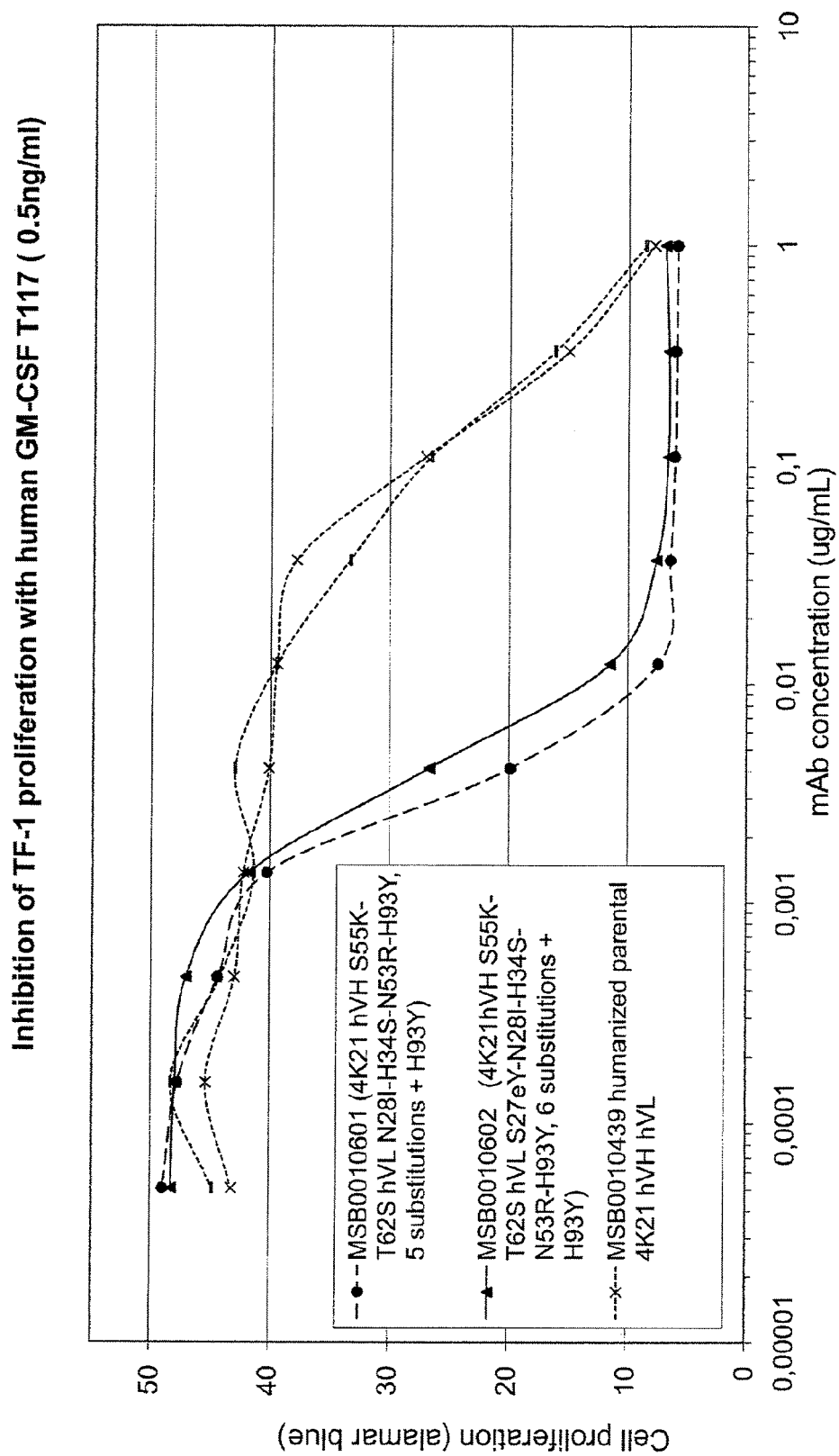
Figure 3C:
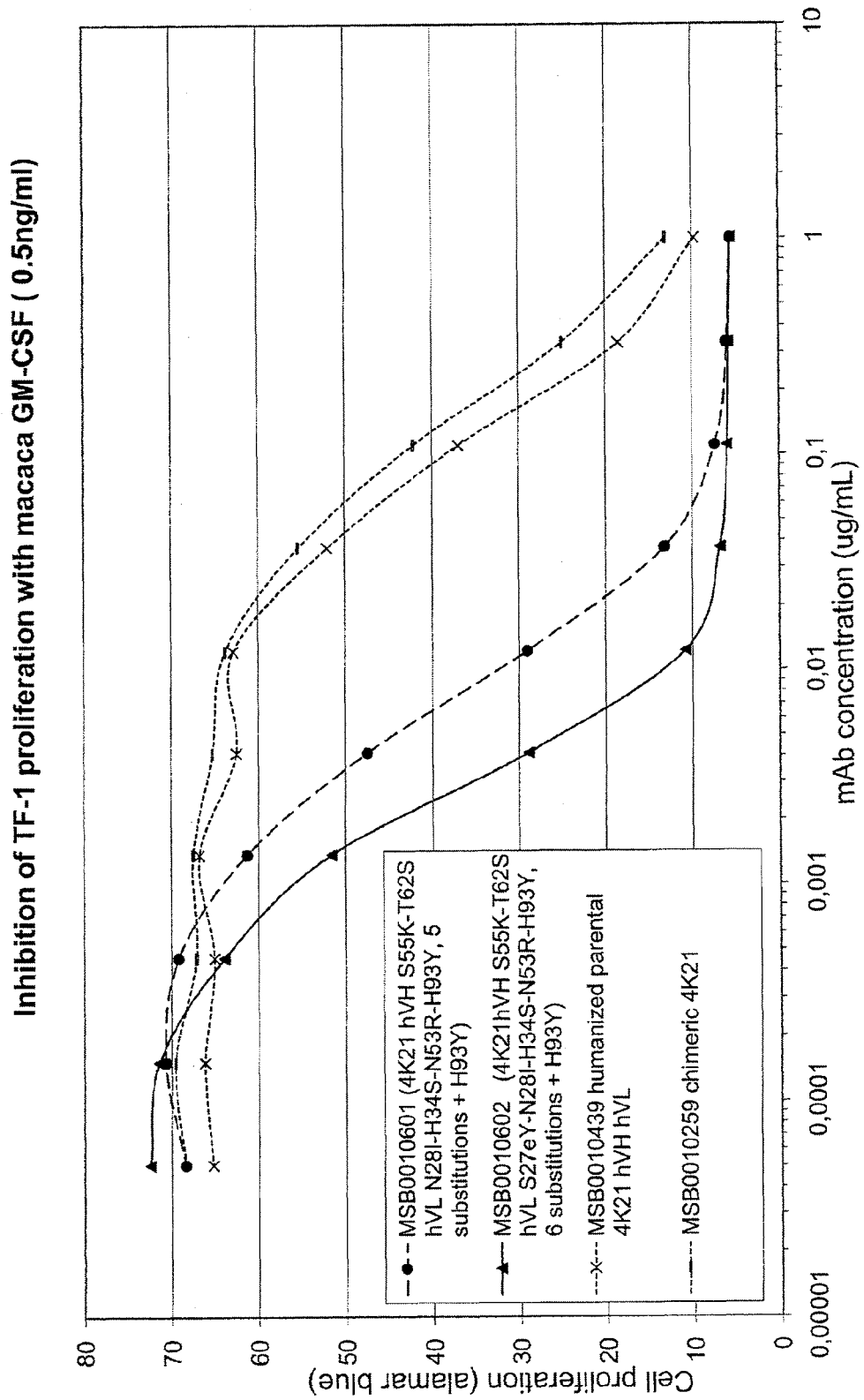

FIG. 3: Inhibition of GM-CSF induced TF-1 proliferation. Dose response of medium-scale purified lead optimized (S55K variants presented here, VL-H93Y with (solid line) and without (dashed line) S27eY mutation), humanized parental and chimeric (dotted line) antibodies were determined for human GM-CSF I117 (FIG. 3a)) and T117 (FIG. 3b)) SNPs and macaca ortholog (32 pM induction; FIG. 3c)). This experiment with average duplicate values is a representative of three.

FIG. 4: Sequence alignment of the optimized 4K21 variable regions compared to the humanized parental hVH and hVL sequences. Beneficial CDR mutations are presented in italics.

Figure 5:
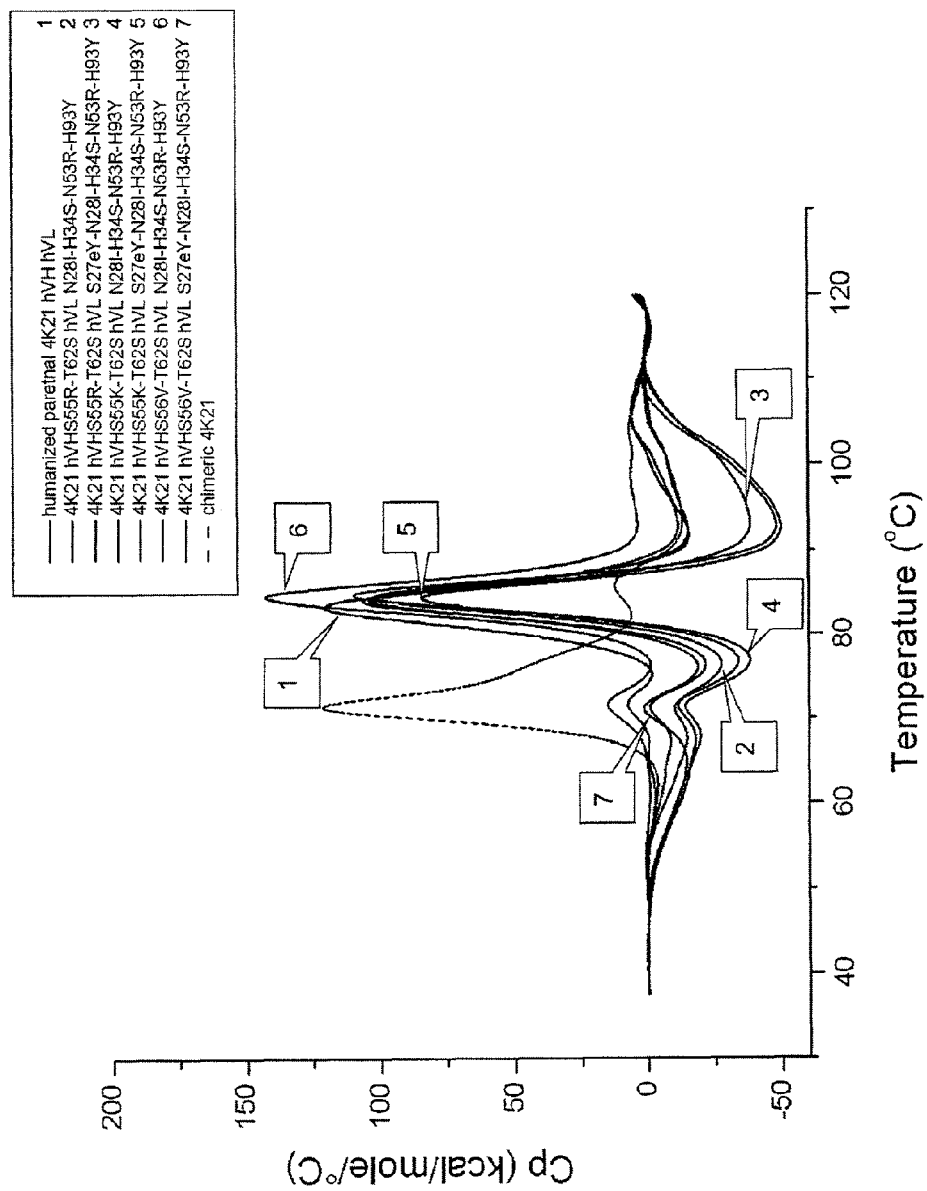

FIG. 5: Melting temperature (Tm) of the Fab by Differential scanning calorimetry (DSC). The Tm of the Fabs appears as second peak, with the exception of the Fab of the chimeric 4K21 antibody (dotted line), for which the Tm overlaps with that of the CH2 domain (first peak).

Figure 6A:
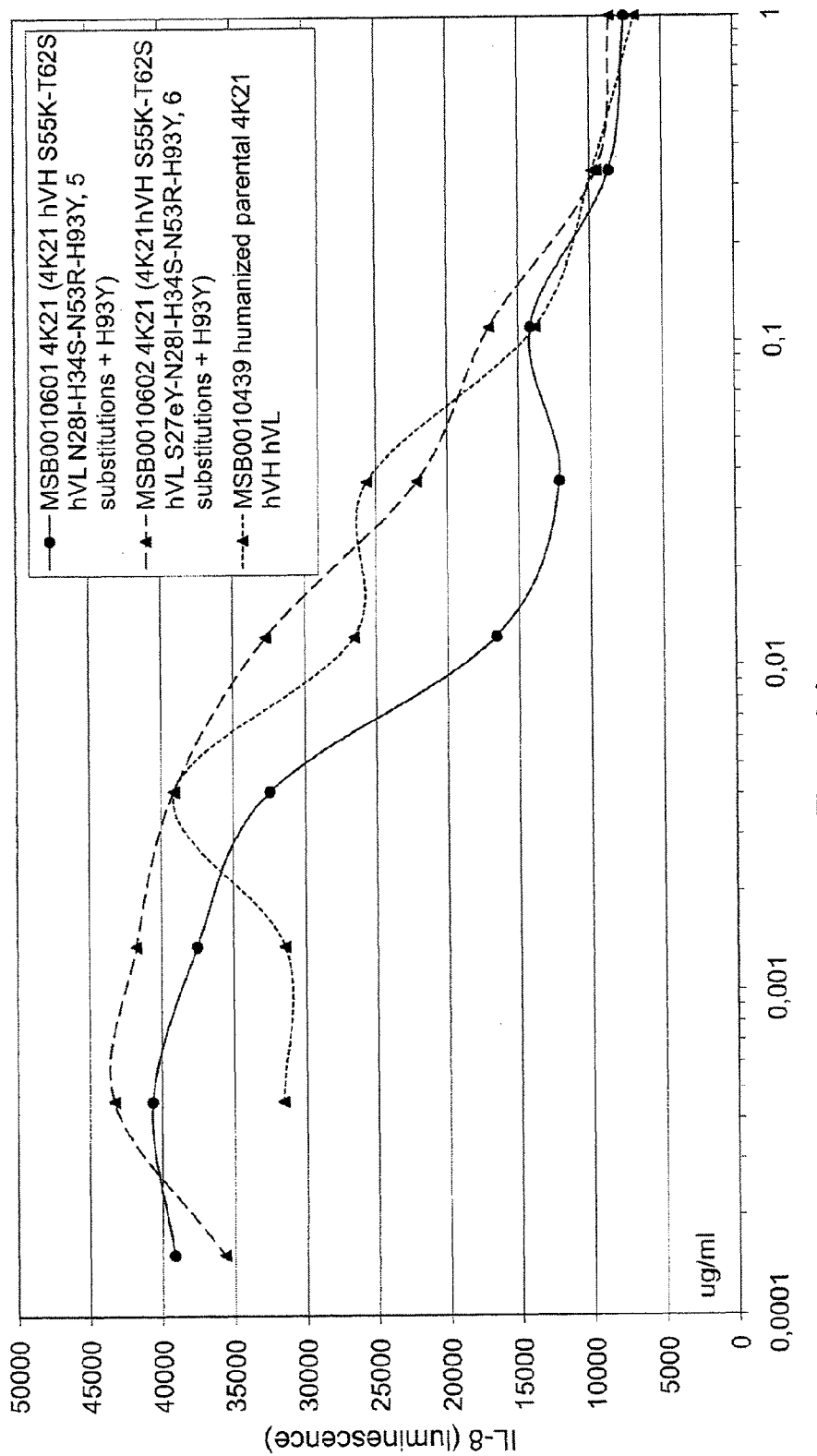

FIG. 6: Inhibition of GM-CSF induced IL-8 secretion in U937 cells. Dose response of medium-scale purified optimized (S55K) variants with H93Y presented with humanized parental 4K21 (dotted line) were determined for human GM-CSF I117 (FIG. 6a)) and B) T117 (FIG. 6b)) SNPs and macaca ortholog (32 pM induction; FIG. 6c)). This experiment is a representative of two.

Figure 7A:
Figure 7B:
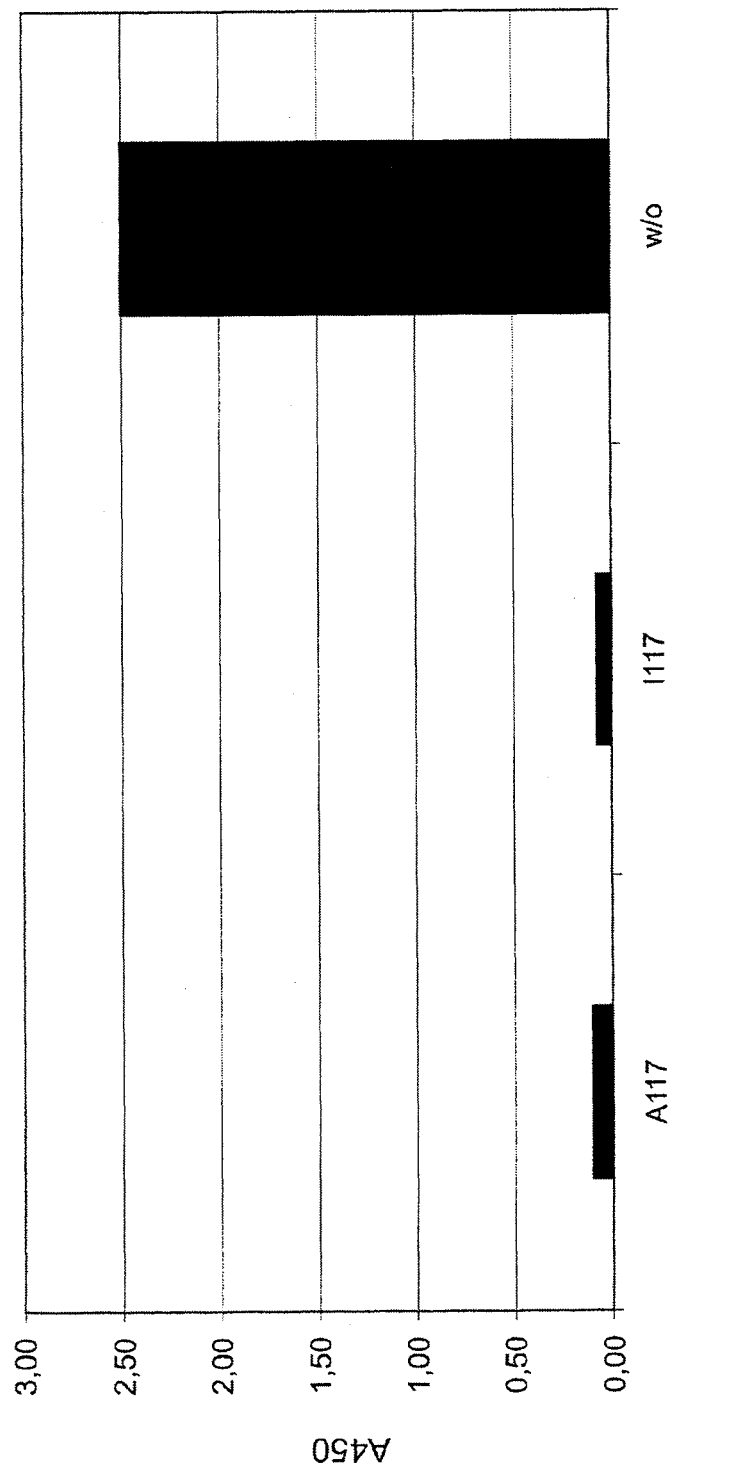

FIG. 7: Anti-GM-CSF ELISA with humanized parental (FIG. 7a)) and optimized 4K21 antibodies (FIG. 7b)) with H93Y (i.e. 4K21 hVH S55K-T62S hVL N28I-H34S-N53R-H93Y and 4K21h VH S55K-T62S hVL S27eY-N28I-H34S-N53R-H93Y) and competition with soluble human GM-CSF containing alanine or isoleucine at position 117. Detection of humanized parental anti-GM-CSF 4K21 binding to coated wild-type GM-CSF is competed away by soluble I117 but not A117. Binding of all optimized 4K21 antibodies to the GM-CSF coated wells is not affected anymore by the presence of A117 protein in solution. Rightmost bar (without competitor GM-CSF (w/o)) shows maximum binding.

Figure 8:
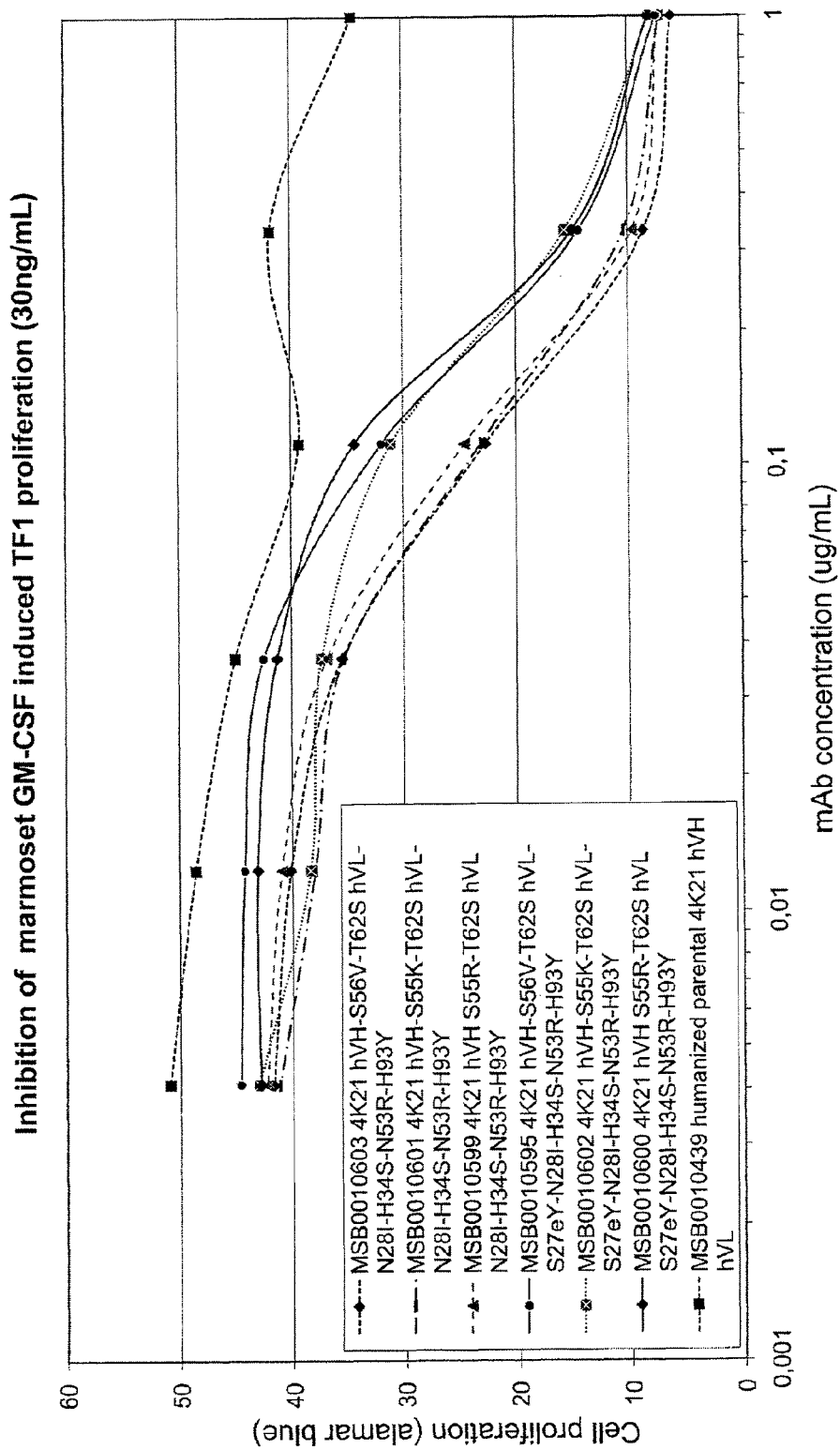

FIG. 8: Inhibition of TF-1 proliferation induced with marmoset monkey GM-CSF. Dose response of small-scale purified optimized S55K, S55R and S56V variant antibodies having VL-H93Y with and without S27eY and humanized parental 4K21 were measured for the inhibition of marmoset GM-CSF (1.92 nM induction). This experiment shows the average duplicate values.

Figure 9A:
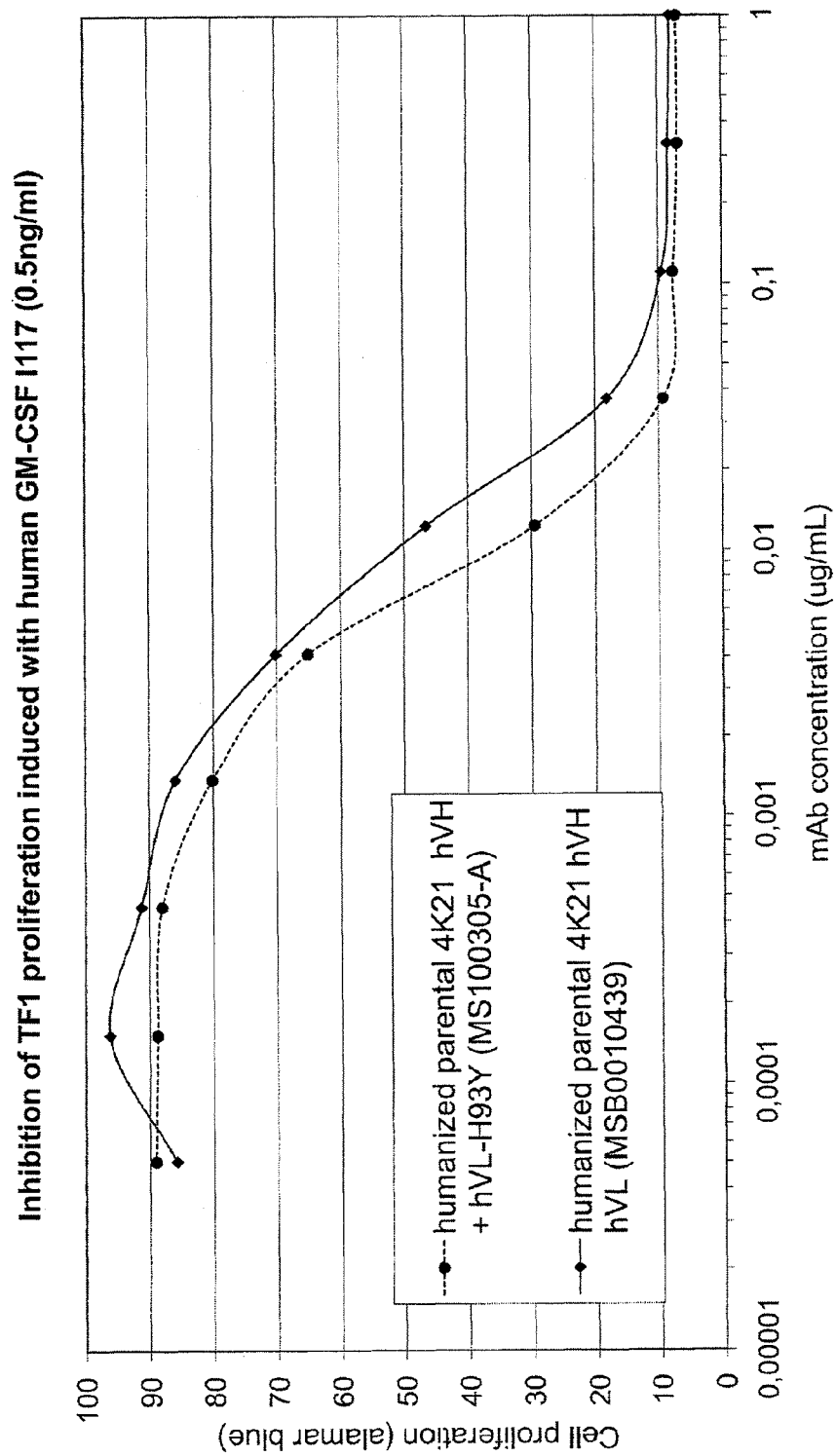
Figure 9B:
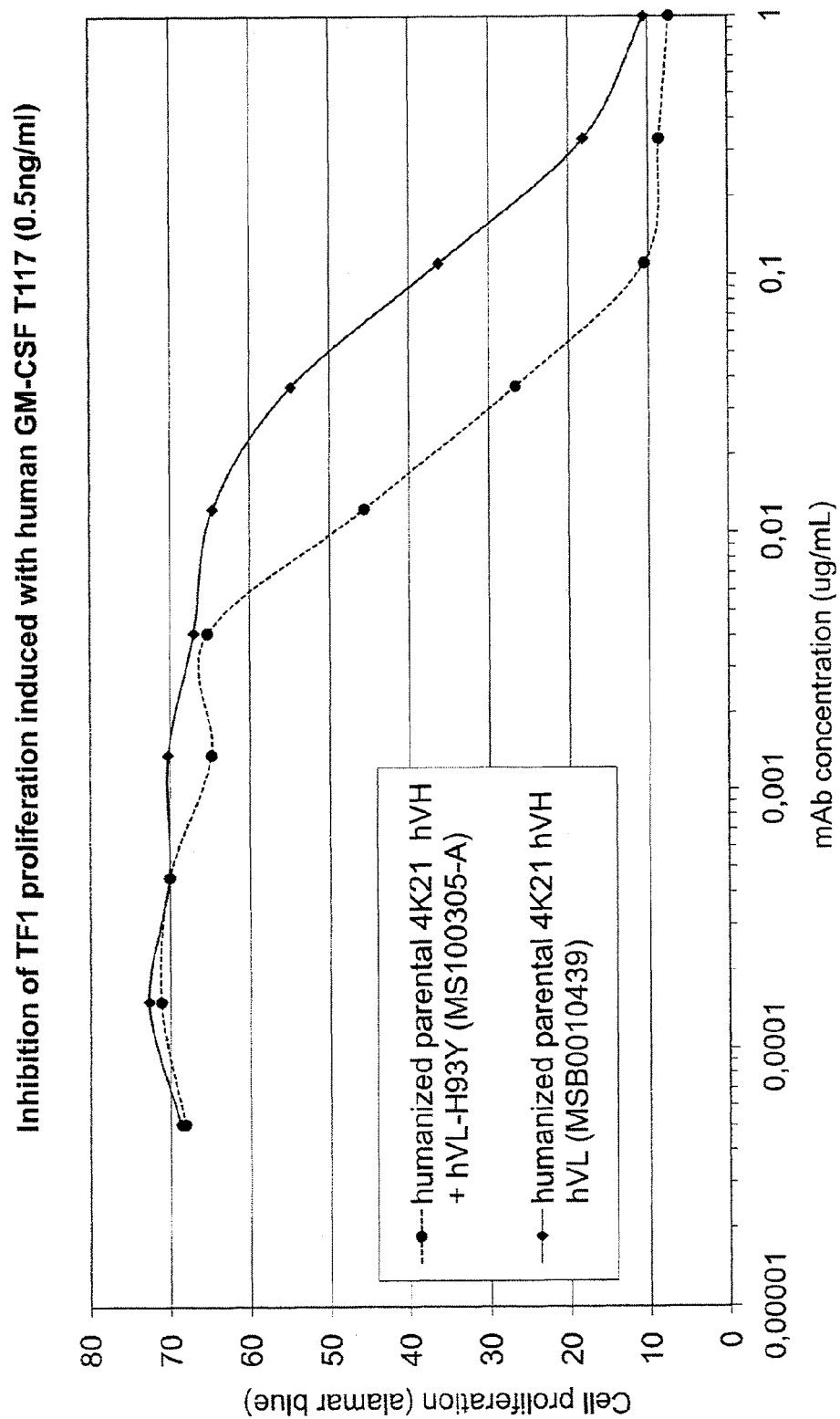
Figure 9C:
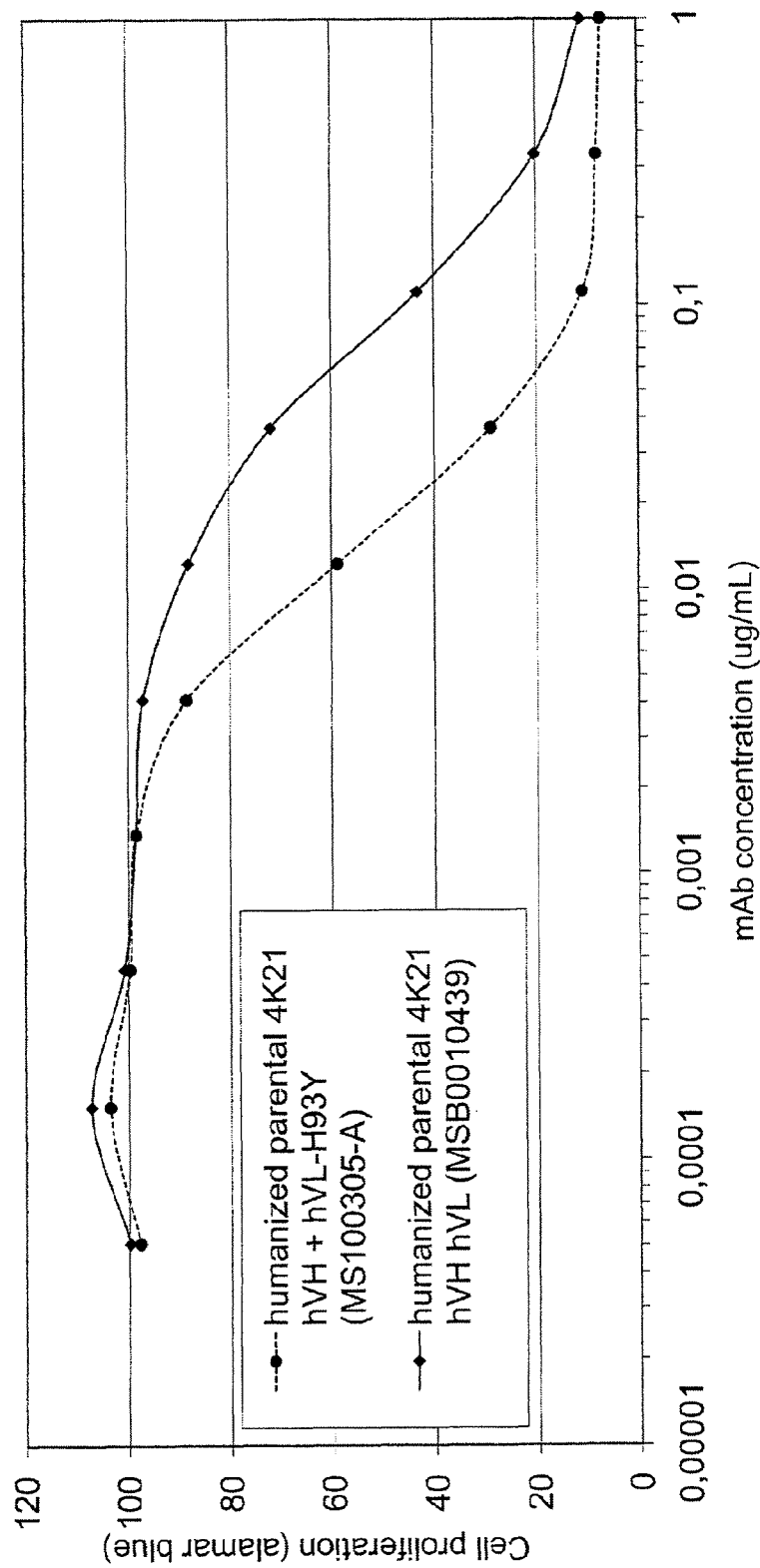

FIG. 9: Inhibition of GM-CSF induced TF-1 proliferation. Dose response of small-scale purified humanized parental 4K21 antibody with (solid line) or without (dotted line) VL-H93Y mutation for the inhibition of human GM-CSF I117 (A) and T117 SNPs (B) and macaca ortholog (C) (32 pM induction). This experiment with average duplicate values is a representative of two.

EXAMPLES

Example 1

Humanization of Murine Monoclonal GM-CSF Antibody 4K21

A recombinant chimeric form of the murine hybridoma-derived 4K21 antibody was obtained by fusing the murine 4K21 variable heavy and light chain DNA sequences (4K21-mVH and -mVL; SEQ ID NOs: 17 and 19) into expression plasmids containing human constant IgG1 heavy chain and kappa light chain domains, respectively. Co-expression of these plasmids resulted in anti-GM-CSF 4K21 hIgG1K antibody (MSB0010259).

Humanization of 4K21 was done by grafting 4K21's murine CDR regions into the frameworks of human VH3 (V-base VH3-07, i.e. IGHV3-7; SEQ ID NO: 24) and VK2 (V-base VK2-A3, i.e. IGKV2-28; SEQ ID NO: 25) germ line genes. Only four back mutations (A28, R44, L47 and T93) to the corresponding murine sequence in the framework were reintroduced in the humanized VH, and none in the VL. The 4K21-VH3-07.1AL heavy chain (4K21-hVH; SEQ ID NO: 18) and 4K21-VK2-A3.2 light chain (4K21-hVL; SEQ ID NO: 20) thus constitute the humanized parental anti-GM-CSF 4K21 VH3-07.1AL+VK2-A3.2 hIgG1K antibody (MSB0010439) (FIG. 2).

To determine potency and affinity of the antibody, $K_d$ measurements and a proliferation bioassay of TF-1 cells were performed. TF-1 is an erythroleukemic cell line from blood, which proliferates in response to e.g. GM-CSF. $K_d$ determination was carried out with the Kinetic Exclusion Assay (KINEXA®; Sapidyne Instruments, Inc., Boise, Id., USA).

In the TF-1 proliferation assay and the KINEXA®, the humanized parental 4K21 antibody (MSB0010439) had a similar potency and affinity to the chimeric (MSB0010259) and murine 4K21 antibody, including the >10× stronger preference for GM-CSF I117 versus T117, and was <10 fold less efficient on neutralizing the orthologs of cynomolgus (*Macaca fascicularis*) and rhesus (*Macaca mulatta*) monkeys.

Example 2

Screening of Mutants and Characterization of Final Lead Optimized 4K21 IgGs in the Inhibition of TF-1 Proliferation Assay During the screening procedure using calibrated IgG supernatants of transiently transfected cells or small-scale purified antibody samples, 9 individual amino acid substitutions at 8 different sites were identified that contribute to the improvement of 4K21: 5 individual VH- & VL-mutations (VH-S55K, S55R or S56V, and VL-N53R and H93Y) partly reduced the human SNP and macaca binding differences and improved overall potency as compared to the parental antibody; VL-H34S improved overall potency for all target species and expression; VL-N28I removed the NG deamidation site without affecting potency; VL-S27eY totally cancelled the macaca ortholog difference and further destroyed the potential NS deamidation site adjacent to NG; and T62S increased homology to human germline gene.

Small-scale purified humanized parental antibody with the H93Y mutant alone (MS100305-A) improved the $IC_{50}$ of the humanized parental 4K21 antibody (MSB0010439) by 2.3-, 6-, and 5-fold in the presence of hGM-CSF-I117, T117, and the macaca ortholog, respectively. Consequently, the affinity for hGM-CSF T117 or macaca GM-CSF were still 3.7- or 2.6-fold lower than for hGM-CSF I117, respectively (FIG. 9 and Table 1a)).

Strikingly, the combination of the above-identified mutations at the following positions: VH-(S55 or S56) and T62 plus VL-S27e, N28, H34, N53 and H93, and pairing of the heavy and light chains in medium scale purified antibody batches reproducibly resulted in total issue resolution and an overall improvement in several respects of the new antibody compared to parental 4K21 (FIG. 3 and Table 1). Three mutations at two different positions (S55K, R55K and S56V) are non-cumulative, and therefore only one is sufficient. Including VL-S27eY greatly reduces the binding difference between the human and the macaca ortholog, but slightly reduces the potency to human GM-CSF isoforms, hence this mutation is optional. Therefore, the final molecules may contain mutations at two VH position (S55K or S55R or S56V) and T62S, plus five VL positions N28I, H34S, N53R, H93Y and S27eY, which is optional, in order to reach a high level of inhibition, almost equally on all GM-CSF species in TF-1 proliferation ($IC_{50}$=20 pM).

In summary, a maximum of seven mutations including H93Y is sufficient to resolve all issues of 4K21, and lead to an overall improvement of the antibody. The sequences and alignments of the optimized 4K21 hVHs and hVLs are presented in FIG. 4.

TABLE 1a

Inhibition of GM-CSF induced TF-1 proliferation

| $IC_{50}$ (pM) Average n = 2-3 (32 pM GM-CSF) | humanized parental 4K21 hVH hVL (MSB0010439) | humanized parental 4K21 hVL + H93Y (MS100305-A) | Fold improvement of humanized parental 4K21 |
|---|---|---|---|
| hGM-CSF (I117) | 98 | 42 | 2.3 |
| STDEV | 23 | 1 | |
| hGM-CSF (T117) | 947 | 154 | 6 |
| STDEV | 154 | 35 | |
| Fold human T117/I117 | 9.7 | 3.7 | |
| macaca GM-CSF | 557 | 111 | 5 |
| STDEV | 120 | 17 | |
| Fold macaca/human I117 | 5.7 | 2.6 | |

TABLE 1b

Inhibition of GM-CSF induced TF-1 proliferation

| $IC_{50}$ (pM) Average n = 3 (32 pM GM-CSF) | MSB0010601 4K21 (4K21 VH S55K-T62S VL N28I-H34S-N53R-H93Y) | MSB0010599 4K21 (4K21 VH S55R-T62S VL N28I-H34S-N53R-H93Y) | MSB0010603 4K21 (4K21 VH S56V-T62S VL N28I-H34S-N53R-H93Y) | MSB0010602 4K21 (4K21 VH S55K-T62S VL S27eY-N28I-H34S-N53R-H93Y) |
|---|---|---|---|---|
| hGM-CSF (I117) | 23 | 18 | 39 | 20 |
| STDEV | 8 | 5 | 19 | 9 |
| hGM-CSF (T117) | 21 | 18 | 34 | 34 |
| STDEV | 5 | 4 | 12 | 13 |
| macaca GM-CSF | 53 | 54 | 82 | 24 |
| STDEV | 12 | 17 | 25 | 10 |
| Fold human T117/I117 | 0.9 | 1.0 | 0.9 | 1.7 |
| Fold macaca/human I117 | 2.3 | 3.0 | 2.1 | 1.2 |
| Fold improvement of humanized parental 4K21 on I117 | 5.3 | 6.7 | 3.1 | 6.0 |
| Fold improvement of humanized parental 4K21 on T117 | 68 | 77 | 42 | 41 |
| Fold improvement of humanized parental 4K21 on macaca | 15 | 15 | 10 | 33 |
| Fold improvement of 4K21 H93Y alone on I117 | 1.3 | 1.6 | 0.8 | 1.5 |
| Fold improvement of 4K21 H93Y alone on T117 | 8.3 | 9.5 | 5.1 | 5.0 |

TABLE 1b-continued

| Inhibition of GM-CSF induced TF-1 proliferation | | | | |
|---|---|---|---|---|
| Fold improvement of 4K21 H93Y alone on macaca | 1.8 | 1.8 | 1.2 | 4.0 |

| $IC_{50}$ (pM) Average n = 3 (32 pM GM-CSF) | MSB0010600 4K21 (4K21 VH S55R-T62S VL S27eY-N28I-H34S-N53R-H93Y) | MSB0010595 4K21 (4K21 VH S56V-T62S VL S27eY-N28I-H34S-N53R-H93Y) | MS100305-A humanized parental 4K21 hVH hVL + H93Y | MSB0010439 humanized parental 4K21 hVH hVL | MSB0010259 chimeric 4K21 |
|---|---|---|---|---|---|
| hGM-CSF (I117) | 33 | 37 | 30 | 121 | 130 |
| STDEV | 11 | 21 | 5 | 62 | 45 |
| hGM-CSF (T117) | 47 | 46 | 172 | 1401 | 1413 |
| STDEV | 15 | 11 | 41 | 395 | 749 |
| macaca GM-CSF | 37 | 44 | 96 | 793 | 1218 |
| STDEV | 14 | 19 | 29 | 164 | 140 |
| Fold human T117/I117 | 1.4 | 1.2 | 5.8 | 11.6 | 10.8 |
| Fold macaca/human I117 | 1.1 | 1.2 | 3.2 | 6.6 | 9.3 |
| Fold improvement of humanized parental 4K21 on I117 | 3.6 | 3.2 | 4.1 | 1.0 | 0.9 |
| Fold improvement of humanized parental 4K21 on T117 | 30 | 30 | 8 | 1.0 | 1.0 |
| Fold improvement of humanized parental 4K21 on macaca | 21 | 18 | 8 | 1.0 | 0.7 |
| Fold improvement of 4K21 H93Y alone on I117 | 0.9 | 0.8 | 1.0 | 0.2 | 0.2 |
| Fold improvement of 4K21 H93Y alone on T117 | 3.6 | 3.7 | 1.0 | 0.1 | 0.1 |
| Fold improvement of 4K21 H93Y alone on macaca | 2.6 | 2.2 | 1.0 | 0.1 | 0.1 |

Example 3

Thermal Stability of Fab Fragments of IgGs by Differential Scanning Calorimetry

The humanized and optimized Fab molecules were showing a melting temperature superior to 84° C. compared to the chimeric 4K21 molecule (Tm=71° C.) as measured by Differential Scanning calorimetry (DSC) (FIG. 5 and Table 2). The Tm of the Fabs appears as second peak, with the exception of the Fab of the chimeric 4K21 antibody, for which the Tm overlaps with that of the CH2 domain (first peak).

TABLE 2

| Fab melting temperature by DSC | | |
|---|---|---|
| Batch ID | antibody | Tm (° C.) |
| MSB0010259 | chimeric 4K21 | 71.4 |
| MSB0010439 | humanized parental 4K21 hVH hVL | 83.3 |
| MSB0010599 | 4K21 (4K21 hVH S55R-T62S hVL N28I-H34S-N53R-H93Y) | 84.5 |
| MSB0010600 | 4K21 (4K21 hVH S55R-T62S hVL S27eY-N28I-H34S-N53R-H93Y) | 84.1 |
| MSB0010601 | 4K21 (4K21 hVH S55K-T62S hVL N28I-H34S-N53R-H93Y) | 84.8 |
| MSB0010602 | 4K21 (4K21hVH S55K-T62S hVL S27eY-N28I-H34S-N53R-H93Y) | 84.5 |
| MSB0010603 | 4K21 (4K21 hVH S56V-T62S hVL N28I-H34S-N53R-H93Y) | 84.5 |

TABLE 2-continued

Fab melting temperature by DSC

| Batch ID | antibody | Tm (° C.) |
|---|---|---|
| MSB0010595 | 4K21 (4K21hVH S56V-T62S hVL S27eY-N28I-H34S-N53R-H93Y) | 84.3 |

Example 4

Affinity in Solution to Human GM-CSF SNPs and Macaca GM-CSF by KINEXA®

The 4K21 and reference antibodies were incubated at concentration below the expected $K_d$ with serial dilutions of human GM-CSF I117 or T117, or macaca GM-CSF up to equilibrium. The remaining free antibody was measured in a Kinetic exclusion assay with the KINEXA® instrument. $K_d$ was calculated by fitting the curve of the signal obtained versus the GM-CSF concentrations. The average of two experiments using different IgG concentrations was calculated. Compared to chimeric (MSB0010259) and humanized parental 4K21 (MSB0010439), the affinity of the optimized 4K21 antibody increased 3- to 5-fold with respect to hGM-CSF I117, 25- to 35-fold with respect to hGM-CSF T117, and 5- to 9-fold with respect to macaca GM-CSF. The affinity differences of the optimized 4K21 antibody between the 2 hGM-CSF isoforms and the macaca ortholog is reduced to less than 3-fold from up to 10-fold for the chimeric 4K21 (Table 3)). The kinetics data is in agreement with $IC_{50}$ data in the TF-1 proliferation assay, i.e. the affinity of the optimized 4K21 antibodies 4K21 hVH S55K-T62S hVL N28I-H34S-N53R plus H93Y is almost equal for all GM-CSF variants ($K_d$=5-12 pM).

TABLE 3

$K_d$ affinity measurement in solution using Kinetic exclusion assay.

| Affinity ($K_d$) using KinExA ® (pM) | | hGM-CSF-I117 MSB0002702 | hGM-CSF-T117 MSB0010388 | macaca GM-CSF MSB0002734 |
|---|---|---|---|---|
| Batch ID | Antibody | H-2 | H-1 | H-2 |
| MSB0010259 | chimeric 4K21 (Ave n = 2) | 17 | 174 | 104 |
| MSB0010439 | humanized parental 4K21 hVH hVL (Ave n = 2) | 21 | 164 | 63 |
| MSB0010601 | 4K21 hVH S55K-T62S hVL N28I-H34S-N53R-H93Y (Ave n = 2) | 6 | 5 | 12 |

Example 5

Inhibition of IL-8 Secretion in U937 Cells

The potency of the optimized antibodies and the humanized parental antibody on the three GM-CSF targets was compared in this assay. Strikingly, the differences in potency observed with the humanized parental 4K21 antibody for the macaca and the human GM-CSF T117 compared to the human GM-CSF I117 target are absent for the optimized antibodies (FIG. 6 and Table 4).

TABLE 4

Inhibition of GM-CSF induced IL-8 secretion in U937 cells

| $IC_{50}$ (pM) (n = 2) (65 pM GM-CSF) | MSB0010601 4K21 (4K21 hVH S55K-T62S hVL N28I-H34S-N53R-H93Y) | MSB0010602 4K21 (4K21hVH S55K-T62S hVL S27eY-N28I-H34S-N53R-H93Y) | MSB0010439 humanized parental 4K21 hVH hVL |
|---|---|---|---|
| human GM-CSF I117 | 334 | 267 | 170 |
| STDEV | 417 | 113 | 150 |
| human GM-CSF T117 | 263 | 177 | 930 |
| STDEV | 265 | 70 | 250 |
| macaca GM-CSF | 340 | 232 | 1120 |
| STDEV | 349 | 7 | 300 |

Example 6

Epitope Mapping of 4K21 to GM-CSF at Position 117

Epitope mapping based on a competition enzyme-linked immunosorbent assay (ELISA) protocol has shown that 4K21 interacts with hGM-CSF through one key residue at position 117. Substitution of this residue with alanine dramatically reduced binding of the parental chimeric or humanized 4K21 antibodies. Mapping the epitope of the lead optimized 4K21 mutants revealed that in all cases they bind equally well to the hGM-CSF A117 mutant as to the naturally occurring hGM-CSF isoforms (FIG. 7). This demonstrates that binding of the optimized 4K21 mAbs to hGM-CSF is independent of the amino acid at position 117 (whether I, T or A), suggesting that optimization has produced a shift in the epitope away from this amino acid.

Example 7

Inhibition of GM-CSF-Induced CD11b Upregulation on Human Neutrophils

Neutrophils from two donors were purified from buffy coats and induced with GM-CSF I117 or T117 in the presence of different anti-GM-CSF antibodies in dose response. After 2 days of incubation, CD11b cell-surface expression was measured by Fluorescence Activated Cell Sorting (FAGS). IC$_{50}$ was single digit nM for optimized antibody 4K21 hVH S55K-T62S hVL N28I-H34S-N53R-H93Y, but not for humanized parental 4K21 on human GM-CSF T117, which was 10-fold worse than on GM-CSF I117 and than other antibodies (Table 5). Interestingly, only the optimized 4K21 antibody showed >80% maximum activity, whereas the humanized parental antibody was only partially inhibiting C011b upregulation.

TABLE 5

Inhibition of CD11b upregulation on neutrophils after GM-CSF stimulation

| antibody | human GM-CSF I117 | | human GM-CSF T117 | |
| --- | --- | --- | --- | --- |
| | IC$_{50}$ (nM) | Emax (%) | IC$_{50}$ (nM) | Emax (%) |
| Humanized parental 4K21 hVH hVL | 3.06 +/− 3.5 | 65 +/− 18 | 31.6 +/− 31 | 68 +/− 6 |
| 4K21 hVH S55K-T62S hVL N28I-H34S-N53R-H93Y | 1.41 +/− 0.6 | 79 +/− 13 | 2.03 +/− 1.4 | 97 +/− 4 |

Example 8

GM-CSF Ortholog Sequences

The rhesus macaque monkey (*Macaca mulatta*) GM-CSF sequence was obtained from Swissprot (Q9GL44_MACMU; SEQ ID NO:29) and the Crab eating cynomolgus macaque monkey (*Macaca fascicularis*) GM-CSF was cloned from cynomolgus monkey lung RNA using RT-PCR primers that are conserved between the 5' and 3' untranslated regions of the human and rhesus GM-CSF mRNA sequences. The amino acid sequences of both rhesus and cynomolgus macaque GM-CSF orthologs are identical.

The human GM-CSF sequence was obtained from Swissprot (CSF2_HUMAN; SEQ ID NO:26) and blasted against the common marmoset (*Callithrix jacchus*) genomic sequences available in GenBank and translated in the 6 frames. The best score was obtained with the contig AC151012 (216132 bp). Using the GeneWise program (see e.g. Birney E, Clamp M, Durbin R. GeneWise and Genomewise. Genome Res. 2004; 14:988-995.), marmoset eDNA and protein sequences were predicted. The human and marmoset protein sequences were aligned and show an identity of 84%. The predicted marmoset protein sequence is now available in Uniprot (BOKWQ4_CALJA; SEQ ID NO:30).

In order to consolidate the gene prediction, the marmoset predicted sequence was aligned with human and rhesus sequences, these 3 sequences are very similar (see FIG. 1b)). The marmoset protein sequence was also blasted against the Uniprot Database, the best hit obtained against a human protein is GM-CSF.

Example 9

Cross-Reactivity and Neutralization of Non-Human Primate Marmoset GM-CSF (*Callithrix jacchus*)

Recombinant marmoset GM-CSF was shown to be active in the TF-1 proliferation assay with an EC$_{50}$ of 90 ng/ml. The potency of the optimized 4K21 antibodies for the neutralization of the marmoset monkey GM-CSF was compared to that of the chimeric and humanized parental 4K21 antibodies. Strikingly, only the optimized 4K21 molecules (i.e. S55K, S55R and S56V hVH T62S variants+hVL N28I-H34S-N53R-H93Y with or without S27eY) were able to neutralize marmoset GM-CSF whereas the parental 4K21 was not (FIG. 8 and Table 6). Therefore, cross-reactivity towards marmoset GM-CSF was gained during optimization and therefore activity of the optimized 4K21 antibodies could be uniquely tested in relevant in vivo pharmacological models—for instance of multiple sclerosis and rheumatoid arthritis—in marmoset monkey.

TABLE 6

Inhibition of marmoset GM-CSF induced TF-1 proliferation (1.9 nM) IC$_{50\ (nM)}$

| | |
| --- | --- |
| MSB0010603 | 0.7 |
| 4K21 hVH-S56V-T62S hVL-N28I-H34S-N53R-H93Y | |
| MSB0010601 | 0.7 |
| 4K21 hVH-S55K-T62S hVL-N28I-H34S-N53R-H93Y | |
| MSB0010599 | 0.9 |
| 4K21 hVH S55R-T62S hVL N28I-H34S-N53R-H93Y | |
| MSB0010595 | 1.5 |
| 4K21 hVH-S56V-T62S hVL-S27eY-N28I-H34S-N53R-H93Y MSB0010602 | 1.3 |
| 4K21 hVH-S55K-T62S hVL-S27eY-N28I-H34S-N53R-H93Y MSB0010600 | 2.0 |
| 4K21 hVH S55R-T62S hVL S27eY-N28I-H34S-N53R-H93Y MSB0010439 | not |
| humanized parental 4K21 hVH hVL | neutralizing |

Example 10

Determination of Properties of an Exemplary 4K21 Humanized Variant

For the anti-GM-CSF antibody humanized variant 4K21 hVH-S55K-T62S hVL-N28I-H34S-N53R-H93Y, greatly improved potency to GM-CSF I117 (5.3×), T117 (68×) and macaca (15× without S27eY, 33× with S27eY as compared to the parental antibody 4K21 has been determined. Further, the potency ratio T/I=0.9×, $^{I117}$IC$_{50}$=23 pM, $^{T117}$IC$_{50}$=21 pM, compared to the parental 4K21 antibody, which had a 11.6× difference for both SNPs.

Furthermore, a better potency on macaca GM-CSF of IC$_{50}$=53 PM with a reduced difference to human I117 (2.3×), compared to the humanized parental 4K21 (6.6×), could be achieved. With the S27eY mutation, the IC$_{50}$ was improved to 24 pM.

Further improved properties include the lack of the potential deamidation site in the light chain CDR1, a high thermal Fab stability (84.8° C.), and a single digit pM affinity for both human GM-CSF SNPs.

The antibodies of the invention are thus not binding anymore to human GM-CSF in a manner dependent to position 117, as exemplified by the 4K21 hVH-S55K-T62S hVL-N28I-H34SN53R-H93Y variant Moreover, these antibodies are thus fully potent on both I117 and T117 GM-CSF SNPs for the inhibition of GM-CSF induced CD11b upregulation in neutrophills, as well as fully cross-reactive to and potently neutralizing marmoset GM-CSF.

The invention claimed is:

1. An isolated antibody comprising
   (i) a heavy chain variable region comprising complementarity determining regions CDR1, CDR2, and CDR3 of SEQ ID NOs: 1, 2, and 3, or variants thereof; and
   (ii) a light chain variable region comprising complementarity determining regions CDR1, CDR2, and CDR3 of SEQ ID NOs: 4, 5 and 6, or variants thereof, with the proviso that the amino acid tyrosine in the light chain CDR3 of SEQ ID NO: 6 is not substituted, which tyrosine is at position 93 of the light chain variable region according to the numbering of Kabat et al,
wherein the variants of the heavy chain variable region or of the light chain variable region or of both the heavy chain variable region and the light chain variable region have one or more amino acids selected from the group consisting of the amino acid
   (a) serine at position 55 (VH S55) in the heavy chain CDR2 is substituted by lysine or arginine,
   (b) serine at position 56 (VH S56), in the heavy chain CDR2 is substituted by valine,
   (c) threonine at position 62 (VH T62) in the heavy chain CDR2 is substituted by serine,
   (d) asparagine at position 28 (VL N28), in the light chain CDR1 is substituted by serine,
   (e) histidine at position 34 (VL H34) in the light chain CDR1 is substituted by isoleucine, and/or
   (f) asparagine at position 53 (VL N53) in the light chain CDR2 is substituted by arginine,
wherein the amino acid positions in the heavy chain CDR2, the light chain CDR1, and light chain CDR2 are according to the numbering of Kabat et al,
   or an antigen-binding fragment thereof, and
wherein said antibody binds to human GM-CSF and the antibody or antigen binding fragment thereof has an affinity to the human GM-CSF T117 and I117 alleles that differs by a factor of less than 5.

2. The antibody according to claim 1, wherein the antibody or antigen binding fragment thereof has a potency on the human GM-CSF T117 and I117 alleles that differs by a factor of less than 5.

3. The antibody according to claim 1, wherein the antibody is a monoclonal, a chimeric, a recombinant, a human or a humanized antibody.

4. The antibody according to claim 1, wherein the amino acid serine at position 27e of the light chain CDR1 is substituted by tyrosine (VL S27eY), wherein the amino acid position in the light chain CDR1 is according to the numbering of Kabat et al.

5. The antibody according to claim 1 comprising
   (i) a variable heavy chain region comprising CDR1 of SEQ ID NO:1, CDR2 of SEQ ID NOs:11, 12, or 13, and CDR3 of SEQ ID NO:3, and
   (ii) a variable light chain region comprising CDR1 of SEQ ID NOs: 14 or 15, CDR2 of SEQ ID NO:16, and CDR3 of SEQ ID NO:6.

6. A pharmaceutical composition comprising the antibody or antigen-binding fragment thereof according to claim 1.

7. The pharmaceutical composition according to claim 6, further comprising pharmaceutically acceptable excipients, adjuvants, diluents, carriers, or combinations thereof.

8. A method for detecting GM-CSF comprising contacting a subject or a sample with the antibody according to claim 1, and detecting or quantifying the presence of GM-CSF in the subject or sample.

9. A method for inhibiting GM-CSF in a subject comprising administering the antibody according to claim 1 to the subject.

10. The method of claim 9, wherein the subject has a disorder associated with elevated levels of GM-CSF, elevated activity of GM-CSF, or combinations thereof.

11. The method of claim 9, wherein the subject has an auto-immune disease or an inflammatory disease.

12. The antibody according to claim 1, wherein the antibody or antigen binding fragment thereof has an affinity that differs by a factor of less than 2.

13. The antibody according to claim 1, wherein the antibody or antigen binding fragment thereof has a potency that differs by a factor of less than 2.

14. The antibody according to claim 1 comprising a variable light chain region of SEQ ID NOs: 8, 9, or 10.

15. The antibody according to claim 1 comprising
   (i) a variable heavy chain region of SEQ ID NOs: 18, 21, 22, or 23, and
   (ii) a variable light chain region of SEQ ID NOs: 8, 9, or 10.

16. The antibody according to claim 15 comprising (i) the variable heavy chain region of SEQ ID NO:21 and (ii) the variable light chain region of SEQ ID NO:10.

17. A nucleic acid encoding the antibody or antigen-binding fragment thereof according to claim 1.

18. A vector or vector system comprising the nucleic acid according to claim 17, and further comprising an expression vector, wherein the nucleic acid is operably linked to one or more expression control sequences.

19. An isolated host cell for expressing the vector or vector system according to claim 18 including the vector or vector system in the non-human host organism or host cell.

20. An isolated host cell for expressing the nucleic acid according to claim 17 including the nucleic in the non-human host organism or host cell.

* * * * *